(12) United States Patent
Kelly et al.

(10) Patent No.: US 11,344,210 B2
(45) Date of Patent: May 31, 2022

(54) DELIVERY CATHETER FOR IMPLANTABLE MEDICAL DEVICE

(71) Applicant: Medtronic, Inc., Minneapolis, MN (US)

(72) Inventors: Tomas K. Kelly, Galway (IE); Paula McDonnell, Galway (IE); Rónán P. Wood, Galway (IE); Declan J. Curran, Shannon (IE)

(73) Assignee: Medtronic, Inc., Minneapolis, MN (US)

( * ) Notice: Subject to any disclaimer, the term of this patent is extended or adjusted under 35 U.S.C. 154(b) by 945 days.

(21) Appl. No.: 15/846,797

(22) Filed: Dec. 19, 2017

(65) Prior Publication Data

US 2018/0168468 A1 Jun. 21, 2018

Related U.S. Application Data

(60) Provisional application No. 62/436,676, filed on Dec. 20, 2016.

(51) Int. Cl.
*A61B 5/0215* (2006.01)
*A61B 5/00* (2006.01)
(Continued)

(52) U.S. Cl.
CPC .......... *A61B 5/02152* (2013.01); *A61B 5/002* (2013.01); *A61B 5/686* (2013.01);
(Continued)

(58) Field of Classification Search
CPC ...................... A61B 5/02; A61B 5/021; A61B 5/1215–02158; A61B 5/027;
(Continued)

(56) References Cited

U.S. PATENT DOCUMENTS 5,372,600 A 12/1994 Beyar et al.
5,772,668 A * 6/1998 Summers .................. A61F 2/88
606/191

(Continued)

OTHER PUBLICATIONS (PCT/US2017/067354) PCT Notification of Transmittal of the International Search Report and the Written Opinion of the International Searching Authority, dated Mar. 28, 2018, 14 pages.

(Continued)

*Primary Examiner* — Jacqueline Cheng
*Assistant Examiner* — Jairo H Portillo
(74) *Attorney, Agent, or Firm* — Shumaker & Sieffert, P.A.

(57) ABSTRACT

A kit for intravascular implantation of an implantable medical device (IMD) within a patient includes the IMD, an elongated shaft, and a locking mandrel. The IMD comprises a fixation assembly comprising a loop and defines at least one longitudinal lumen and a port in fluid communication with the lumen. The shaft is sized to traverse a vasculature of the patient. The port is sized to receive at least a portion of the loop. The locking mandrel is configured to be positioned within the at least one lumen of the shaft and to pass through the loop within the lumen at the port. A reduced profile portion of the shaft defines a reduced profile with respect to at least one other portion of the shaft. At least a portion of the reduced profile portion is configured to be adjacent to the IMD when the IMD is positioned on the shaft.

7 Claims, 21 Drawing Sheets

(51) Int. Cl.
*A61M 25/09* (2006.01)
*A61M 25/00* (2006.01)
*A61B 17/34* (2006.01)
*A61N 1/36* (2006.01)
*A61N 1/372* (2006.01)
*A61N 1/39* (2006.01)

(52) U.S. Cl.
CPC ..... *A61B 17/3468* (2013.01); *A61M 25/0023* (2013.01); *A61M 25/09* (2013.01); *A61N 1/36* (2013.01); *A61N 1/372* (2013.01); *A61N 1/3956* (2013.01)

(58) Field of Classification Search
CPC ..... A61B 5/058; A61B 5/145; A61B 5/14503; A61B 5/6852–686; A61B 17/3468; A61B 2017/347; A61M 25/00; A61M 25/0023; A61M 25/09; A61M 25/09016–0905
See application file for complete search history.

(56) References Cited

U.S. PATENT DOCUMENTS

| | | | |
|---|---|---|---|
| 6,562,064 | B1 | 5/2003 | DeBeer |
| 8,021,307 | B2 | 9/2011 | White et al. |
| 8,355,777 | B2 | 1/2013 | White et al. |
| 8,727,996 | B2 | 5/2014 | Allan et al. |
| 8,864,676 | B2 | 10/2014 | Beasley et al. |
| 2003/0125790 | A1* | 7/2003 | Fastovsky ............ A61B 5/6862 623/1.11 |
| 2006/0200030 | A1 | 9/2006 | White |
| 2006/0200031 | A1* | 9/2006 | White .................. A61B 5/03 600/486 |
| 2007/0049847 | A1* | 3/2007 | Osborne ............ A61M 25/09 600/585 |
| 2007/0112407 | A1 | 5/2007 | Mertens et al. |
| 2008/0221657 | A1* | 9/2008 | Laroya ................. A61F 2/885 623/1.12 |
| 2008/0300607 | A1* | 12/2008 | Meade ............ A61B 17/06066 606/119 |
| 2011/0144560 | A1* | 6/2011 | Gagner ................ A61B 17/221 604/8 |
| 2012/0271134 | A1* | 10/2012 | Allan ..................... A61B 5/686 600/373 |
| 2013/0253309 | A1 | 9/2013 | Allan |
| 2013/0253345 | A1 | 9/2013 | Griswold et al. |
| 2013/0253347 | A1 | 9/2013 | Griswold et al. |
| 2016/0287334 | A1 | 10/2016 | Grant |
| 2016/0310703 | A1 | 10/2016 | Drake et al. |

OTHER PUBLICATIONS

Response to Office Action dated Nov. 21, 2019, from U.S. Appl. No. 15/477,163, filed Feb. 11, 2020, 13 pp.

U.S. Appl. No. 15/477,163, filed by Tomas K. Kelly et al., filed Apr. 3, 2017.

Office Action from U.S Appl. No. 15/477,163, dated Nov. 21, 2019, 13 pp.

First Office Action and Search Report, and machine translation thereof, from counterpart Chinese Application No. 201780077032.3, dated Aug. 2, 2021, 14 pp.

* cited by examiner

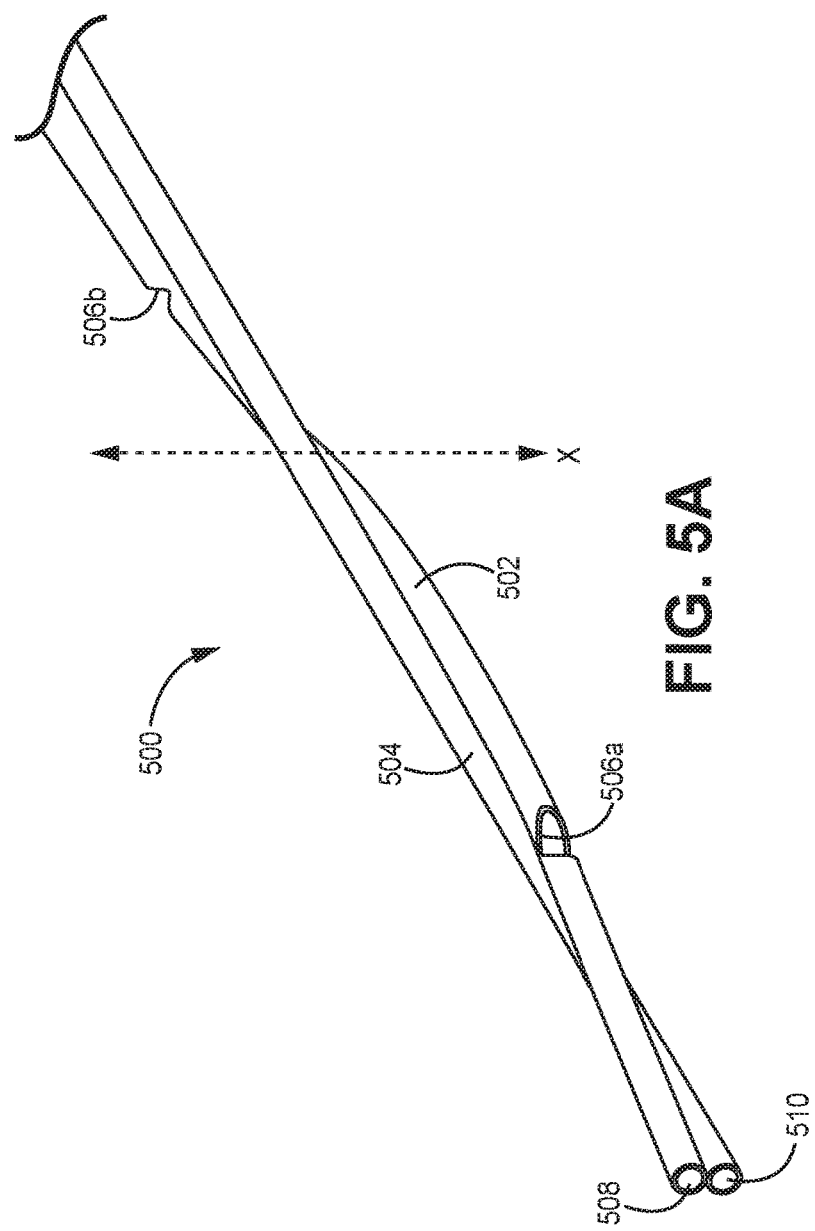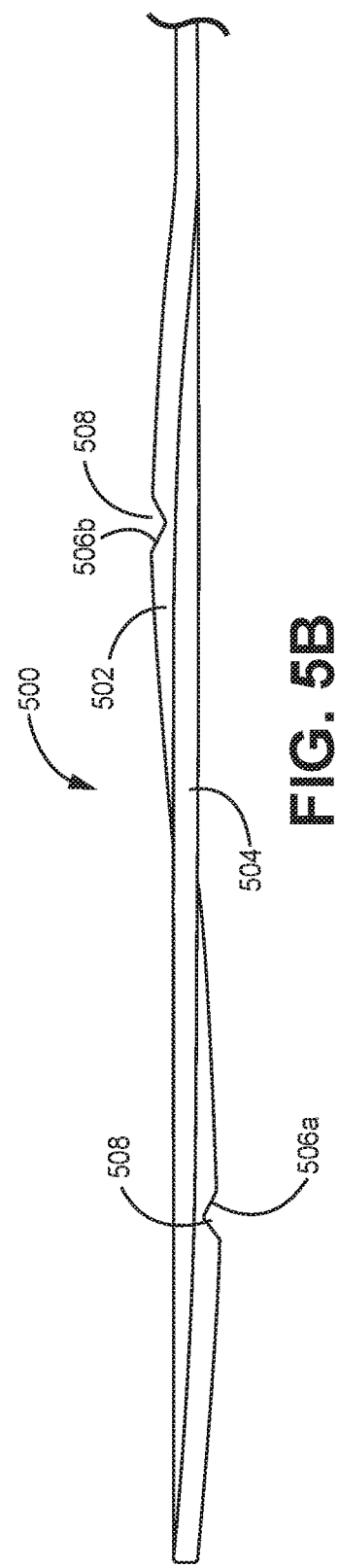

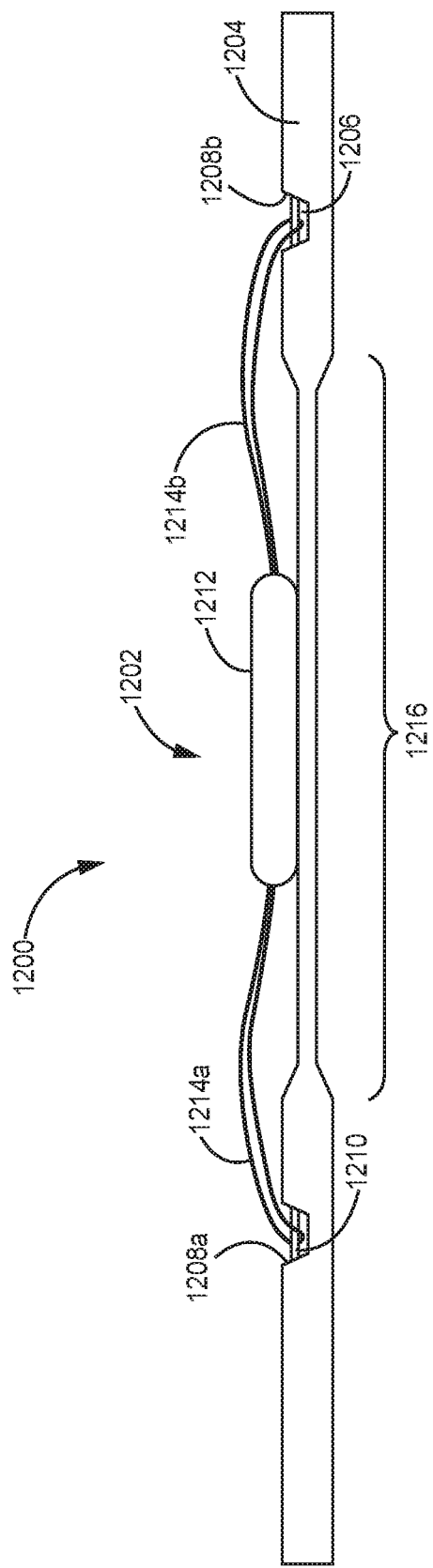

DELIVERY CATHETER FOR IMPLANTABLE MEDICAL DEVICE

CROSS-REFERENCE TO RELATED APPLICATIONS

The present invention claims priority to U.S. Provisional Patent Application No. 62/436,676, entitled "Separable Monitoring Device and Method", filed Dec. 20, 2016, which is incorporated by reference in its entirety.

TECHNICAL FIELD

The disclosure relates to medical devices and, more particularly, devices for delivering implantable medical devices.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads for placing electrodes or sensors at target locations, or may be leadless. Such devices may also have the ability to wirelessly transmit data either to another device implanted in the patient or to another device located externally of the patient, or both. Although implantation of some devices requires a surgical procedure other devices may be small enough to be delivered and placed at an intended implant location in a relatively noninvasive manner, such as by a percutaneous delivery catheter.

By way of illustrative example, implantable miniature sensors have been proposed and used in blood vessels to measure directly the diastolic, systolic and mean blood pressures, as well as body temperature and cardiac output. Such direct in vivo measurement of physiological parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, particularly patients suffering from chronic heart failure, may benefit from the use of implantable sensors adapted to monitor blood pressures. Promising indications have been reported for using such implantable sensors.

SUMMARY

The disclosure describes delivery catheters, systems, and associated techniques, structures, and assemblies for delivery of implantable devices within the body of the patient. In an aspect, delivery catheters are described that may provide improved kink resistance (and thus improved maneuverability) and more accurate deployment than other catheter designs including an outer sheath and/or a balloon for retaining the sensor in place and/or for deploying the sensor.

In one example, a kit for intravascular implantation of an implantable medical device within a patient comprises the implantable medical device, and elongated shaft, and a locking mandrel. The implantable medical device comprises a fixation assembly comprising a loop. The elongated shaft defines at least one longitudinal lumen and a port in fluid communication with the lumen. The shaft is sized to traverse a vasculature of the patient and the port is sized to receive at least a portion of the loop of the fixation assembly of the implantable medical device. The locking mandrel is configured to be positioned within the at least one lumen of the shaft and is configured to pass through the loop of the fixation assembly of the implantable medical device within the lumen at the port. A reduced profile portion of the shaft defines a reduced profile with respect to at least one other portion of the shaft. At least a portion of the reduced profile portion is configured to be adjacent to the implantable medical device when the implantable medical device is positioned on the shaft.

In another example, a kit for intravascular implantation of an implantable medical device within a patient comprises an elongated shaft and a locking mandrel. The elongated shaft defines at least one longitudinal lumen and a port in fluid communication with the lumen. The shaft is sized to traverse a vasculature of the patient and the port is sized to receive at least a portion of a loop of a fixation assembly of the implantable medical device. The locking mandrel is configured to be positioned within the at least one lumen of the shaft and is configured to pass through the loop of the fixation assembly of the implantable medical device within the lumen at the port.

In a further aspect, a method for intravascular implantation of an implantable medical device within a patient comprises positioning a distal end of an assembly at a target vascular location for implantation of an implantable medical device and moving a locking mandrel to release the implantable medical device. The assembly includes the implantable medical device, and elongated shaft, and the locking mandrel. The implantable medical device comprises a fixation assembly comprising a loop. The elongated shaft defines at least one longitudinal lumen and a port in fluid communication with the lumen. The shaft is sized to traverse a vasculature of the patient and the port is sized to receive at least a portion of the loop of the fixation assembly of the implantable medical device. The locking mandrel is positioned within the at least one lumen of the shaft and passes through the loop of the fixation assembly of the implantable medical device within the lumen at the port.

In an additional example, a kit for intravascular implantation of an implantable medical device within a patient comprises an elongated shaft and a locking mandrel. The elongated shaft defines at least one longitudinal lumen and a distal opening of the at least one longitudinal lumen at a distal end of the shaft. The shaft is sized to traverse a vasculature of the patient. The locking mandrel is configured to be positioned within the at least one lumen of the shaft and defines a hook configured to pass through a loop of a fixation assembly of the implantable medical device proximate the distal opening.

In a further example, a kit for intravascular implantation of an implantable medical device within a patient comprises the implantable medical device, an elongated shaft, and a locking mandrel. The implantable medical device comprises a fixation assembly comprising a first loop and a second loop. The elongated shaft defines at least one longitudinal lumen, a proximal port in fluid communication with the lumen, and a distal port in fluid communication with the lumen. The shaft is sized to traverse a vasculature of the patient. The proximal port is sized to receive at least a portion of the first loop of the fixation assembly of the implantable medical device. The distal port is sized to receive at least a portion of the second loop of the fixation assembly of the implantable medical device. Each of the proximal port and the distal port are defined on a side wall of the elongated shaft. The proximal port is circumferentially spaced approximately 180 degrees about the elongated shaft from the distal port. The locking mandrel is configured to be positioned within the at least one lumen of the shaft and is configured to pass through the first loop of the fixation assembly of the implantable medical device within the lumen at the proximal port and to pass through the second loop of the fixation assembly of the implantable medical device within the lumen at the distal port. A reduced profile portion of the shaft defines a reduced profile with respect to at least one other portion of the shaft. At least a portion of the reduced profile portion is configured to be adjacent to the implantable medical device when the implantable medical device is positioned on the shaft.

It should be understood that although the disclosure is described principally in the context of delivering a sensor in a blood vessel, the disclosure is not limited to use in that context. The principles of the disclosure may be used to deliver implantable sensors assemblies adapted to measure and monitor any of a variety of physiological parameters or to medical devices for delivery of therapy.

The details of one or more examples of the invention are set forth in the accompanying drawings and the description below. Other features, objects, and advantages of the invention will be apparent from the description and drawings, and from the claims.

BRIEF DESCRIPTION OF THE DRAWINGS

FIGS. 5A and 5B illustrate perspective and side views of a portion of an example of an elongated shaft of a kit for intravascular implantation of an implantable medical device within a patient.

FIG. 12 illustrates a side view of a portion of another example kit for intravascular implantation of an implantable medical device within a patient.

DETAILED DESCRIPTION

The present disclosure describes catheter-based systems for delivering miniaturized devices that sense various physiological parameters of a patient such as blood pressure. Such miniaturized devices include implantable medical devices that may comprise a hermetic housing that contains a battery and electronics, and a fixation assembly. The delivery catheter is provided to interface with the sensor device for accurately and efficiently delivering the sensor device. The design of the delivery catheter provides flexibility, thus providing efficient delivery through the vascular structure which includes tortuous pathways defined by the blood vessels of the patient. The design of the delivery catheter also provides more accurate delivery of the sensor device at the target site compared to other designs requiring retraction of an outer sheath and/or a balloon with respect to the sensor device, which may lead to undesired movement the sensor device during or after deployment.

This disclosure will describe delivery assemblies in the context of delivering a pressure sensing miniaturized device. However, it should be understood that the delivery devices may be used in conjunction with other types of miniaturized devices such as temperature sensors, cardiac output sensors, or therapy delivery devices such as pacemakers and drug delivery devices.

In various examples, a delivery assembly formed in accordance with this disclosure may provide one or more advantages. For example, the delivery assemblies may have reduced dimensions and be composed of more desirable (e.g., flexible) materials for tracking through vasculature compared to delivery systems requiring an outer sheath to secure an IMD to a delivery catheter. For example, such dimensions and composition may result in greater kink resistance. This may be particularly important, for example, for delivery to the pulmonary artery. Tracking from the Right Ventricle, through the pulmonary valve, and into the pulmonary artery (an approximately 90 degree turn), may result in unpredictable kinking which may be reduced or eliminated by the described delivery assemblies.

In addition, the described delivery assemblies may result in more accurate deployment. Other assemblies may require that an IMD be pushed out of an outer sheath and that a balloon be retracted proximally past the IMD, which may result in distal migration of the IMD. The delivery assemblies describe herein may eliminate the need for an outer sheath and/or a balloon, thus eliminating this potential migration.

Figure 1A:
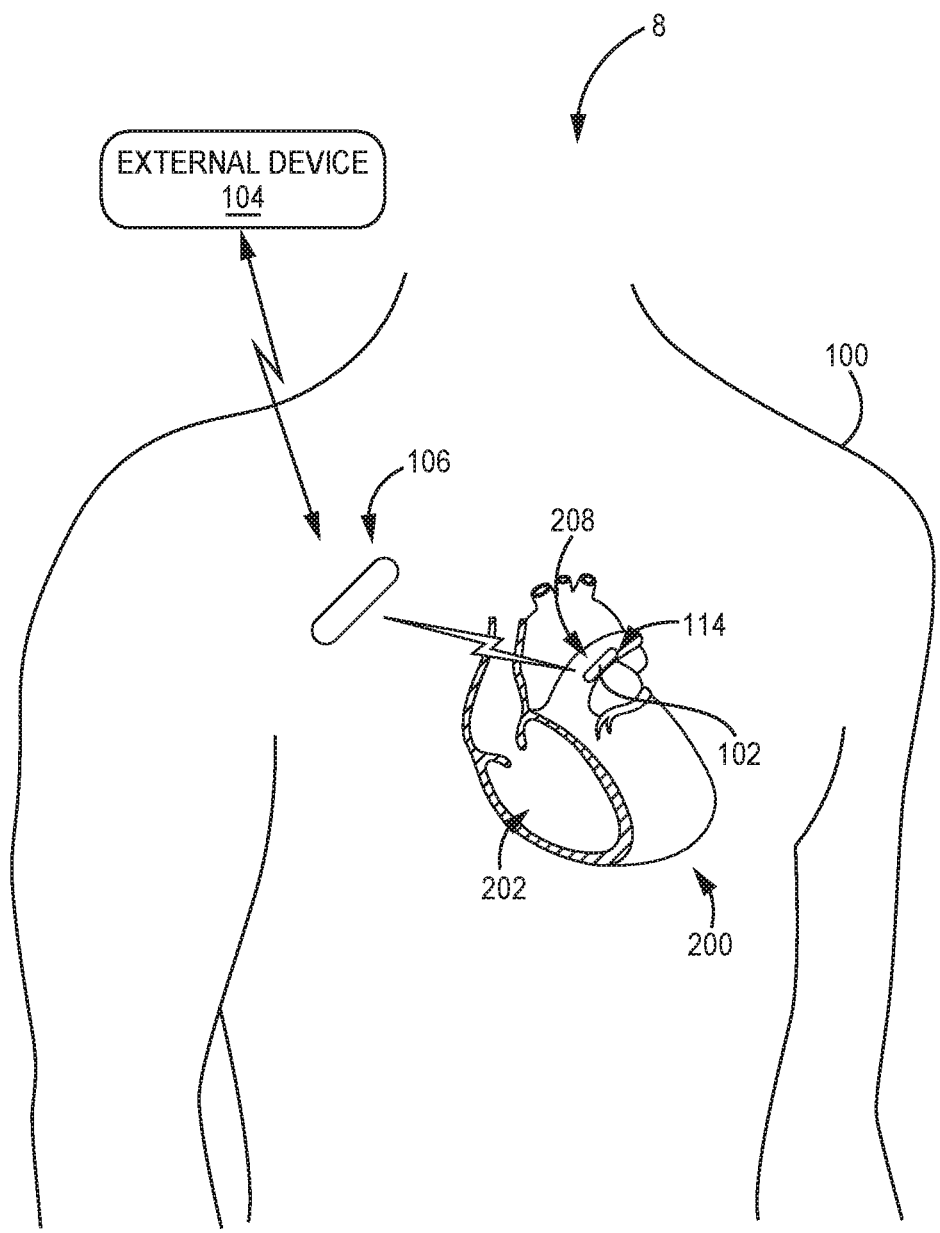
FIG. 1A illustrates, diagrammatically, an example of a patient with implanted medical devices.

FIG. 1A illustrates, diagrammatically, an example of a patient 100 with implanted medical devices including a sensor assembly 114 implanted, for example, in the patient's left pulmonary artery 208 through which blood flows from heart 200 to the lungs, and another device, such as an implantable or insertable cardiac monitor, an implantable hub device or the like, referred to as IMD 106. For purposes of this description, knowledge of cardiovascular anatomy is presumed and details are omitted except to the extent necessary or desirable to explain the context of the invention.

Medical device system 8 is an example of a medical device system configured to monitoring cardiovascular parameters and/or other physiological parameters of patient 100. In the illustrated example, medical device system 8 includes an implantable medical device (IMD) 106, which may comprise an implantable or insertable cardiac monitor or an implantable hub device, in communication with external device 104. Medical device system 8 also includes implantable sensor assembly 114, which comprises sensing device 102. As shown in FIG. 1A, implantable sensor assembly 114 may be implanted within pulmonary artery 208 of heart 200.

In the illustrated example, IMD 106 comprises an insertable cardiac monitor (ICM) configured to sense and record cardiac electrogram (EGM) signals from a position outside of heart 200, and will be referred to as ICM 106 hereafter. In some examples, ICM 106 includes or is coupled to one or more additional sensors, such as accelerometers, that generate one or more signals that vary based on patient motion, posture, blood flow, or respiration. ICM 106 may monitor a physiological parameter such as posture, heart rate, activity level, and/or respiration rate, and may do so at times when the one or more additional sensors, such as sensing device 102, is measuring a patient parameter such as cardiovascular pressure or any other suitable patient parameter. ICM 106 may be implanted outside of the thoracic cavity of patient 100, e.g., subcutaneously or submuscularly, such as at the pectoral location illustrated in FIG. 1A. In some examples, ICM 106 may take the form of a Reveal LINQ™ ICM, available from Medtronic plc, of Dublin, Ireland.

Sensing device 102 may be implanted within a pulmonary artery 208 of patient 100 and may include sensing circuitry configured to measure a parameter of patient 100. For example, sending device 102 may include pressure sensing circuitry configured to measure cardiovascular pressure of patient 100. Each of sensing device 102 and ICM 106 may include a timer and processing circuitry configured to determine a time of day based on the timer value. If sensing device 102 determines that the current time is within a predetermined window that may be stored in memory of sensing device 102, sensing device 102 may measure a parameter of patient 100, which may be contemporaneously or later transmitted to ICM 106. In some examples, sensing device 102 may include wireless communication circuitry configured to receive a trigger signal from ICM 106, e.g., instead of or in addition to the timer and processing circuitry to independently determine when to make a measurement of a patient parameter. In such examples, processing circuitry of sensing device 102 may be configured to control the sensing circuitry of sensing device 102 to measure the patient parameter of patient 100 in response to receiving the trigger signal. In this manner, ICM 106 may dictate the times at which sensing device 102 measures a patient parameter, and sensing device 102 may enter a low-power mode such as sleep mode until the wireless communication circuitry of sensing device 102 receives a trigger signal.

ICM 106 may transmit data, including, for example, posture data and/or other physiological parameter data acquired by ICM 106, to external device 104. ICM 106 also may transmit measurements received from sensing device 102 to external device 104. For example, ICM 106 may transmit data related to cardiovascular pressure, posture, heart rate, activity level, respiration rate, and/or other physiological parameters to external device 104. External device 104 may be a computing device configured for use in settings such as a home, clinic, or hospital, and may further be configured to communicate with ICM 106 via wireless telemetry. For example, external device 104 may be coupled to a remote patient monitoring system, such as Carelink®, available from Medtronic plc, of Dublin, Ireland. External device 104 may, in some examples, comprise a programmer, an external monitor, or a consumer device such as a smart phone.

External device 104 may be used to program commands or operating parameters into ICM 106 for controlling its functioning, e.g., when configured as a programmer for ICM 106. External device 104 may be used to interrogate ICM 106 to retrieve data, including device operational data as well as physiological data accumulated in the memory of ICM 106. The accumulated physiological data may include, for example, cardiovascular pressure generally, such as one or more of a systolic pressure, a diastolic pressure, and a mean pulmonary artery pressure, or medians of such pressures, and/or other forms of physiological data. In some examples, the interrogation may be automatic, e.g., according to a schedule. In other examples, the interrogation may occur in response to a remote or local user command. Programmers, external monitors, and consumer devices are examples of external devices 104 that may be used to interrogate ICM 106.

Examples of wireless communication techniques used by ICM 106 and external device 104 include radiofrequency (RF) telemetry, which may be an RF link established via an antenna according to Bluetooth, WiFi, or medical implant communication service (MICS), or transconductence communication (TCC), which may occur via electrodes of ICM 106. Examples of wireless communication techniques used by ICM 106 and sensing device 102 may also include RF telemetry or TCC. In one example, ICM 106 and sensing device 102 communicate via TCC, and ICM 106 and external device 104 communicate via RF telemetry.

Medical device system 8 is an example of a medical device system configured to monitor a cardiovascular parameters of patient 100 and may additionally or alternatively include other medical devices. For example, some additional or alternative medical devices that may be used include external devices configured to monitor posture, heart rate, activity level, respiration rate, and/or other physiological parameters. Although not illustrated in the example of FIG. 1A, medical device system 8 may include one or more implanted or external medical devices in addition to or instead of ICM 106 and sensing device 102. For example, a medical device system may include a vascular ICD or pacemaker (e.g., IMD 16 illustrated in FIG. 1B), an extravascular ICD, or an intracardiac pacemaker. One or more such devices may generate physiological signals, and may include processing circuitry configured to perform, in whole or in part, the techniques described herein for monitoring cardiovascular pressure. In some examples, the implanted devices may communicate with each other and/or with external device 104.

For sake of clarity, sensor assembly 114 is shown without a fixation assembly in FIG. 1A. A suitable fixation assembly configured to secure sensor assembly 114 within pulmonary artery 208 will be discussed below with respect to FIGS. 2A and 2B. The sensor device 102 of the sensor assembly 114 also may communicate wirelessly with the external device 104, either directly or via device 106, to provide in vivo data for selected physiological parameters to an external site to inform clinicians of the patient's status. Although not depicted, sensor device 102 may include wireless communication capabilities, such as low frequency or radiofrequency (RF) telemetry, transconductance communication (TCC), or other wireless communication techniques that allow sensor device 102 to communicate with device 106, external device 104, or another device.

Sensor assembly 114 may be a leadless assembly, e.g., need not be physically coupled to an IMD or other device via a lead, and need not otherwise be coupled to any leads. Although illustrated as being located in the pulmonary artery 208, in some examples, sensory assembly 114 may be located in the right ventricle 202, aorta, and/or other locations within the pulmonary and systemic circulatory systems of patient 100. Sensor assembly 114 may be affixed to the wall of the pulmonary artery 208 or, as another example, the wall of the right ventricle 202. In some examples, pulmonary artery 208 of heart 200 may comprise a left pulmonary artery, whereas in other examples, pulmonary artery 208 may comprise a right pulmonary artery.

Figure 1B:
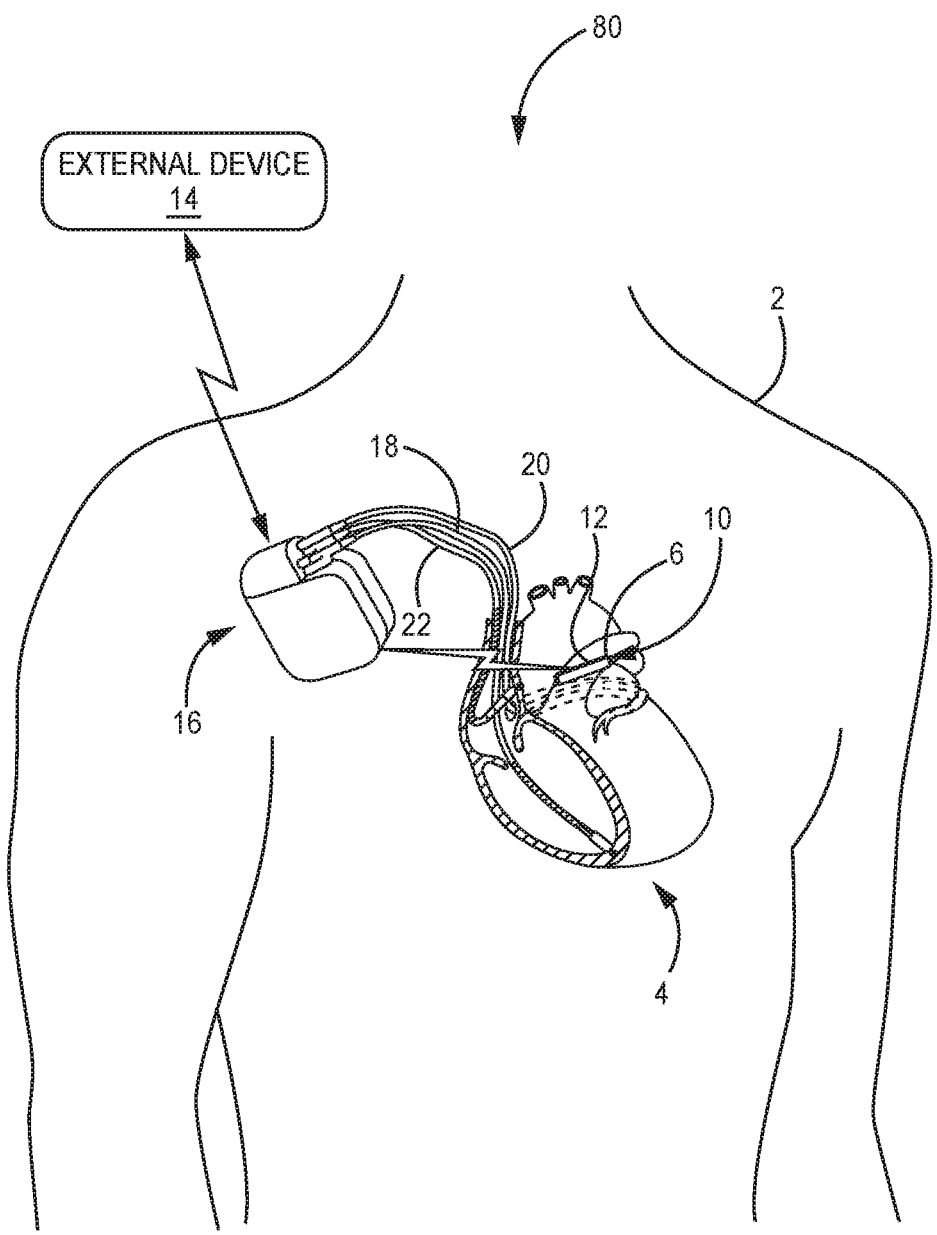
FIG. 1B illustrates, diagrammatically, another example of a patient with implanted medical devices.

FIG. 1B illustrates, diagrammatically, an example of a patient 2 with implanted medical devices including a sensor assembly 10 implanted, for example, in the patient's left pulmonary artery 12 through which blood flows from heart 4 to the lungs, and another device, such as a pacemaker, defibrillator or the like, referred to as IMD 16. For purposes of this description, knowledge of cardiovascular anatomy is presumed and details are omitted except to the extent necessary or desirable to explain the context of the invention.

Medical device system 80, including implantable sensor assembly 10 and IMD 16, is another example of a medical device system configured to implement to monitor cardiovascular parameters. The implantable pressure sensing device 6 of assembly 10, IMD 116, and external device 14 in FIG. 1B may provide substantially similar functionality as the like numbered devices described above with respect to FIG. 1A.

In some examples, IMD 16 may include one or more leads 18, 20, 22 that carry electrodes that are placed in electrical contact with selected portions of the cardiac anatomy in order to perform the functions of IMD 16 as is well known to those skilled in the art. For example, IMD 16 may be configured to sense and record cardiac EGM signals via the electrodes on leads 18, 20, 22. IMD 16 may also be configured to deliver therapeutic signals, such as pacing pulses, cardioversion shocks, or defibrillation shocks, to heart 4 via the electrodes. In the illustrated example, IMD 16 may be a pacemaker, cardioverter, and/or defibrillator.

In some examples, this disclosure may refer to IMD 16, particularly with respect to its functionality as part of a medical device system that monitors cardiovascular pressure and other physiological parameters of a patient 2, as an implantable monitoring device or implantable hub device. In some examples, IMD 16 includes or is coupled to one or more additional sensors, such as accelerometers, that generate one or more signals that vary based on patient motion and/or posture, blood flow, or respiration. IMD 16 may monitor posture of patient 2 at or near the times when implantable pressure sensing device 6 is measuring a cardiovascular parameter such as, for example, cardiovascular pressure.

IMD 16 also may have wireless capability to receive and transmit signals relating to the operation of the device. IMD 16 may communicate wirelessly to an external device, such as external device 14, and/or to another implanted device such as implantable sensing device 6 of the sensor assembly 10, e.g., as described above with respect to IMD 106, external device 104, and sensing device 102 of FIG. 1A. In some examples, an implantable sensing device 6 may communicate wirelessly and directly with an external device 14, rather than communicating with the external device 14 through the IMD 16.

Medical device system 80 is an example of a medical device system configured to monitor a cardiovascular parameter of patient 2 and may perform similar functions to the medical device system 8 of FIG. 1A described above.

For sake of clarity, sensor assembly 6 is shown without a fixation assembly in FIG. 1B. A suitable fixation assembly configured to secure sensor assembly 6 within pulmonary artery 12 will be discussed below with respect to FIGS. 2A and 2B. The sensor device 6 of the sensor assembly 10 also may communicate wirelessly with the external 14, either directly or via device 16, to provide in vivo data for selected physiological parameters to an external site to inform clinicians of the patient's status. Although not depicted, sensor device 6 may include wireless communication capabilities, such as low frequency or radiofrequency (RF) telemetry, transconductance communication (TCC), or other wireless communication techniques that allow sensor device 6 to communicate with device 16, external device 14, or another device.

Sensor assembly 10 may be a leadless assembly, e.g., need not be physically coupled to an IMD or other device via a lead, and need not otherwise be coupled to any leads. Although illustrated as being located in the pulmonary artery 12, in some examples, sensory assembly 10 may be located in the right ventricle, aorta, and/or other locations within the pulmonary and systemic circulatory systems of patient 2. Sensor assembly 10 may be affixed to the wall of the pulmonary artery 12 or, as another example, the wall of the right ventricle. In some examples, pulmonary artery 12 of heart 4 may comprise a left pulmonary artery, whereas in other examples, pulmonary artery 12 may comprise a right pulmonary artery.

Figure 2A:
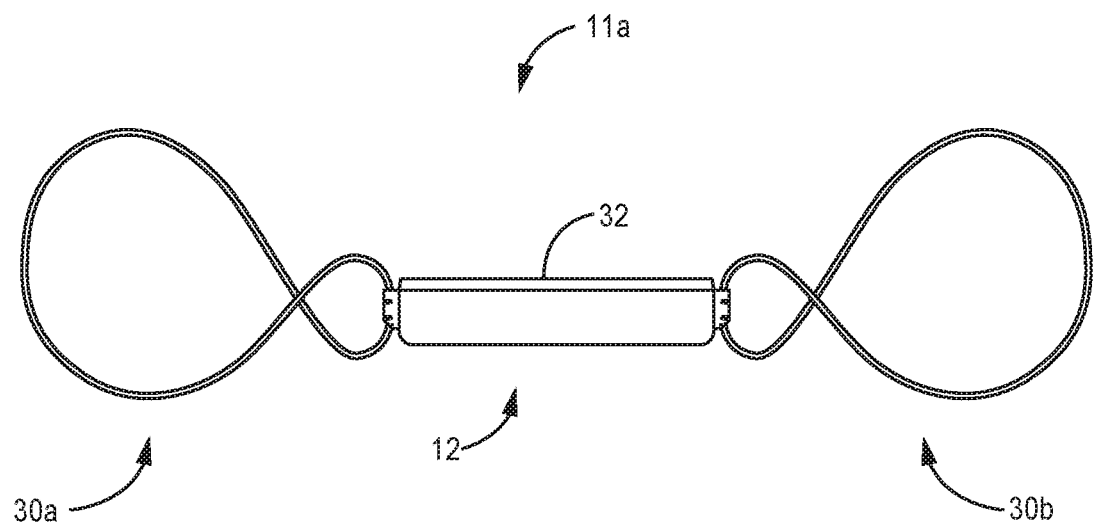
FIGS. 2A and 2B are side profile views of respective example configurations of a sensor assembly.
Figure 2B:
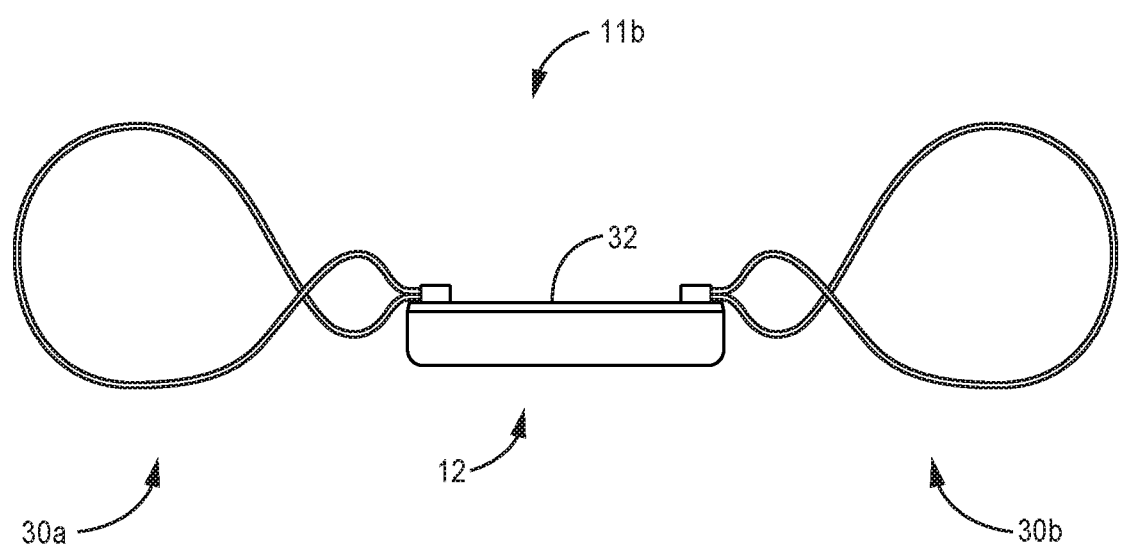

FIGS. 2A and 2B are side profile views of example configurations of a sensor assembly; sensor assembly 11a and sensor assembly 11b (collectively "sensor assembly 10"). The sensor assembly 10 includes a sensor 12 coupled to fixation members 30a, 30b (collectively "fixation assembly 30"). The fixation assembly 30 and sensor 12 are arranged to enable the sensor assembly 10 to be provided in a delivery configuration that enables it to be navigated to an implant location where it can be deployed into the deployment configuration. As described in this disclosure, it should be understood that the delivery configuration defines a pitch, width or diameter that is narrower, in relation to the deployment configuration, along a common plane. Upon release, the fixation assembly expands into the deployment configuration so as to be in physical contact with the wall of the blood vessel to maintain the positional integrity of sensor 12. In one example, the fixation assembly will engage the interior wall of the vessel defining the blood flow lumen. The sensor 12 is attached to the fixation assembly 30 in a manner such that the sensing element 32 of the sensor 12 is spaced from the wall of the vascular lumen to minimize adverse obstruction to blood flow through the lumen and to position the sensing element 32 of the sensor 12 to be fully exposed to the blood in the vessel, without obstruction from the housing of the sensor 12 or the vessel wall.

Figure 3A:
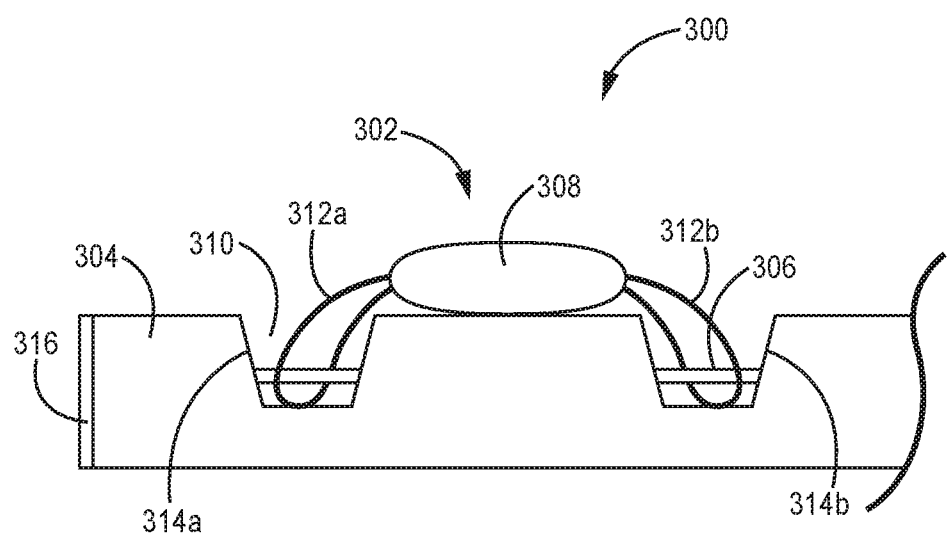
FIGS. 3A and 3B illustrate side profile and side cross-sectional views of a portion of an example kit for intravascular implantation of an implantable medical device within a patient.
Figure 3B:
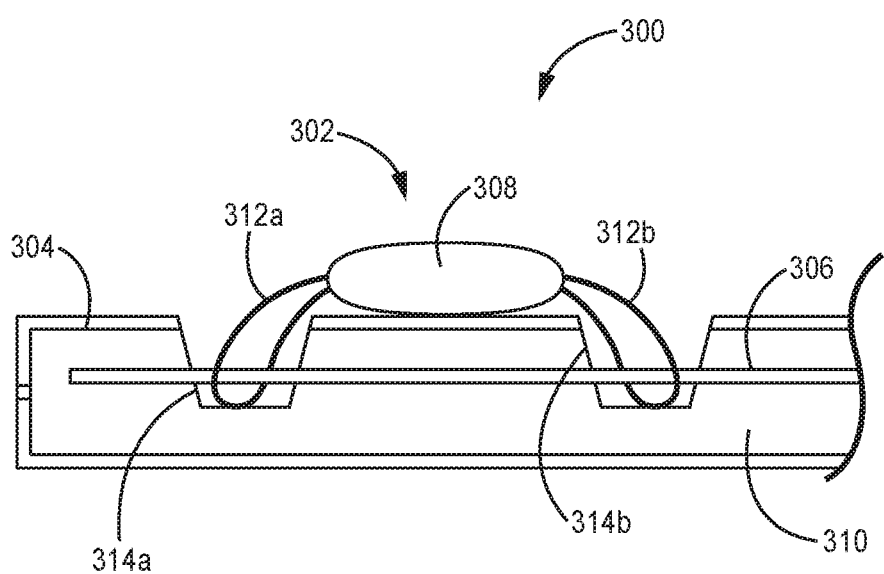

FIGS. 3A and 3B illustrate side profile and side cross-sectional views of a portion of an example kit 300 for intravascular implantation of an implantable medical device (IMD) 302 within a patient. The IMD 302 may be, for example, a sensor assembly, such as the sensor assemblies 114, 10, 11a, and 11b of FIGS. 1A-2B. The kit 300 may include an elongated shaft 304 and a locking mandrel 306. In some examples, the kit 300 may further include the IMD 302.

The IMD 302 may include a housing 308 and a fixation assembly 312. The fixation assembly 312 may include, for example, two fixation members 312a and 312b which may each form a loop. The fixation members 312a and 312b may comprise nitinol or any other suitable material.

The elongated shaft 304 may be sized to traverse a vasculature of the patient and may define a longitudinal lumen 310 and one or more ports 314 in fluid communication with the lumen 310. Although the lumen 310 is shown as being a single lumen, the lumen 310 as described herein may refer to any suitable number of lumens 310. Each of the ports 314a and 314b may be sized to receive at least a portion of a respective loop of the fixation assembly 312 of the IMD 302. The ports 314 may include a proximal port 314b and a distal port 314a, each defined on a side wall of the elongated shaft elongated shaft 304.

The locking mandrel 306 may be configured to be positioned within the lumen 310 of the shaft 304 and may be configured to pass through one or more of the loops of the fixation assembly 312 of the IMD 302 within the lumen 310 at the respective port 314a and/or 314b to secure the IMD 302 to the shaft 304.

In some examples, the kit 300 may additionally include a guidewire (not shown). The locking mandrel 306 may define a guidewire lumen configured for passage of the guidewire. In some examples, the lumen 310 may be configured such that the guidewire and the locking mandrel 306 may be positioned adjacent to one another within the lumen 310.

In some examples, the shaft 304 may be a braided stainless steel wire shaft. In some examples, the shaft 304 may include a jacket comprising a thermoplastic elastomer. The jacket may have decreasing durometer from proximal end to distal end to increase the flexibility of the distal portion of the shaft 304. The outer diameter of the shaft 304 may be approximately 1.5-1.75 mm and an inner diameter of the shaft 304 may be approximately 1.25-1.3 mm.

In some examples, the ports 314 may be positioned in a distal portion of the shaft 304 that is approximately 60-80 mm long.

When the IMD 302 is secured to the shaft 304 by the locking mandrel 306, with housing 308 of IMD 302 outside of the shaft 304, the outer diameter of the kit 300, including the IMD 302, may be less than approximately 4.3-4.45 mm and an introducer sheath of approximately 4.62-5.3 mm inner diameter may be used with the kit 300.

In some examples, the locking mandrel 306 may include or be coupled to a handle mechanism to allow for a practitioner to manipulate the locking mandrel 306 including, for example, advancing the locking mandrel 306 with respect to the shaft 304 and through the loops of the fixation assembly 312 to secure the IMD 302 to the shaft 304 or to retract the locking mandrel 306 with respect to the shaft 304 to release the loops of the fixation assembly 312 and release the IMD 302 from the shaft 304. The handle may comprise an injection molded polymer and may include locking and unlocking functions to lock the locking mandrel 306 in place and release the locking mandrel for movement by the practitioner, respectively. The handle may comprise a male luer threadably fixed to a proximal end of the shaft 304, which may facilitate delivery of the kit via an over the wire method and/or a saline flush prior to introducing the kit into the vasculature.

In some examples, the locking mandrel 306 may comprise a braided shaft. In some examples, the locking mandrel 306 may comprise a polymer extrusion. In some examples, the locking mandrel 306 may have an outer diameter of approximately 0.17-0.25 mm and may be configured to run alongside a guidewire in the lumen 310. In some examples, the locking mandrel 306 may have an outer diameter of approximately 0.8-0.9 mm and an inner diameter of approximately 0.6-0.65 mm may be configured to receive a guidewire.

In some examples, the shaft 304 may comprise a marker band 316 at a distal portion of the shaft 304 which may, comprise, for example, a gold radiopaque ribbon section, a barium sulphate filled thermoplastic elastomer extrusion, and/or a tungsten marker band and may assist a practitioner in visualizing the end of the shaft 304. The marker band 316 may comprise, for example, approximately 60% barium sulphate. Although marker band 316 shown at a distal end of the shaft 304, alternatively or in addition, one or more marker bands may be placed in any suitable location, including proximate one or more of the ports 314, proximate a portion of the shaft 304 configured to be adjacent to the IMD 302 when the IMD is secured to the shaft 304, and/or any other suitable location as may assist a clinician in visualizing and positioning the kit 300 and implanting the IMD 302 within the vasculature of a patient.

Figure 4:
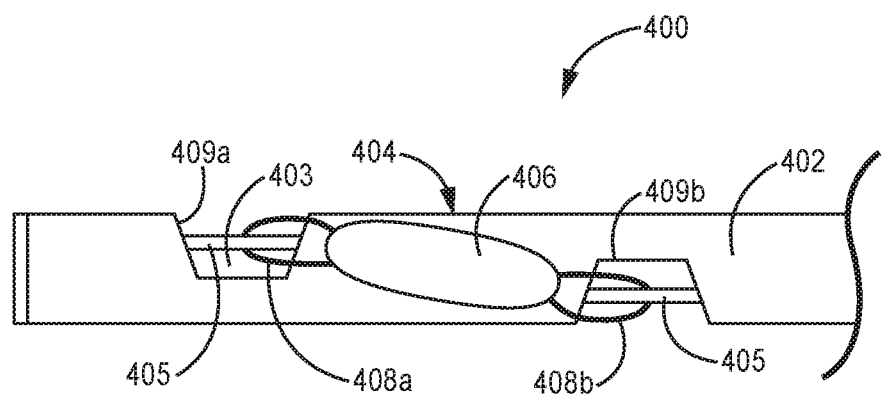
FIG. 4 illustrates a side profile view of a portion of another example kit for intravascular implantation of an implantable medical device within a patient.

FIG. 4 illustrates a side profile view of a portion of another example kit 400 for intravascular implantation of an implantable medical device (IMD) 404 within a patient. The kit 400 may be similar to that of FIGS. 3A and 3B and may include an elongated shaft 402, sized to traverse a vasculature of the patient and defining a lumen 403, a distal port 409a, and a proximal port 409b. The kit 400 may also include a locking mandrel 405, and an IMD 404, including a housing 406 and a fixation assembly 408 including fixation members 408a and 408b, each forming a loop. The IMD 404 may be, for example, a sensor assembly, such as the sensor assemblies 114, 10, 11a, and 11b of FIGS. 1A-2B.

The locking mandrel 405 may be configured to be positioned within the lumen 403 of the shaft 402 and may be configured to pass through one or more of the loops of the fixation assembly 408 of the IMD 404 within the lumen 403 at the respective port 409a and/or 409b to secure the IMD 404 to the shaft 402.

In some examples, the locking mandrel 405 may comprise a braided shaft. In some examples, the locking mandrel 405 may comprise a polymer extrusion. In some examples, the locking mandrel 405 may have an outer diameter of approximately 0.17-0.25 mm and may be configured to run alongside a guidewire in the lumen 403. In some examples, the locking mandrel 405 may have an outer diameter of approximately 0.8-0.9 mm and an inner diameter of approximately 0.6-0.65 mm may be configured to receive a guidewire.

The proximal port 409b may be circumferentially spaced approximately 175-185 degrees about the shaft 402 from the distal port 409a. The circumferential spacing of ports 409 may allow for the IMD 404 to be more tightly secured to the shaft 402, e.g., by providing a greater linear distance between the ports 409, which may reduce the overall profile of the kit 400. In addition, the circumferential spacing of the ports 409 may reduce strain on the fixation members 408a and 408b of the IMD 404.

FIGS. 5A and 5B illustrate perspective and side views of a portion of an example of an elongated shaft 500 of a kit for intravascular implantation of an implantable medical device (IMD) within a patient. The shaft 500 may be similar to the shafts 304 and 402 described with reference to FIGS. 3A-4 and may be configured to be used in a similar manner. The shaft 500 may be sized to traverse a vasculature of a patient.

The shaft 500 may include a locking shaft 502 and a guidewire shaft 504. The locking shaft 502 may define one or more ports 506a and 506b (collectively "ports 506") and a locking lumen 508 configured to receive a locking mandrel. The guidewire shaft 504 may define a guidewire lumen 510 configured to receive a guidewire (not shown).

As illustrated in FIGS. 5A and 5B, the locking shaft 502 may be twisted about the guidewire shaft 504 such that the proximal port 506b may be circumferentially spaced approximately 175-185 degrees about the shaft 500 from the distal port 506a. The circumferential spacing of ports 506 may allow for an IMD to be more tightly secured to the kit including the shaft 500, e.g., by providing a greater linear distance between the ports 506, which may reduce the overall profile of the kit. In addition, the circumferential spacing of the ports 506 may reduce strain on the fixation members of the IMD.

Twisting of the locking shaft 502 about the guidewire shaft 504, as well as the circumferential spacing of the ports 506, may allow an IMD to be located at a low profile portion of the shaft 500 such that the overall profile of the kit, including the IMD, may be reduced.

In some examples, the outer diameter of the shaft 500 may be approximately 2.0-2.6 mm.

Figure 6:
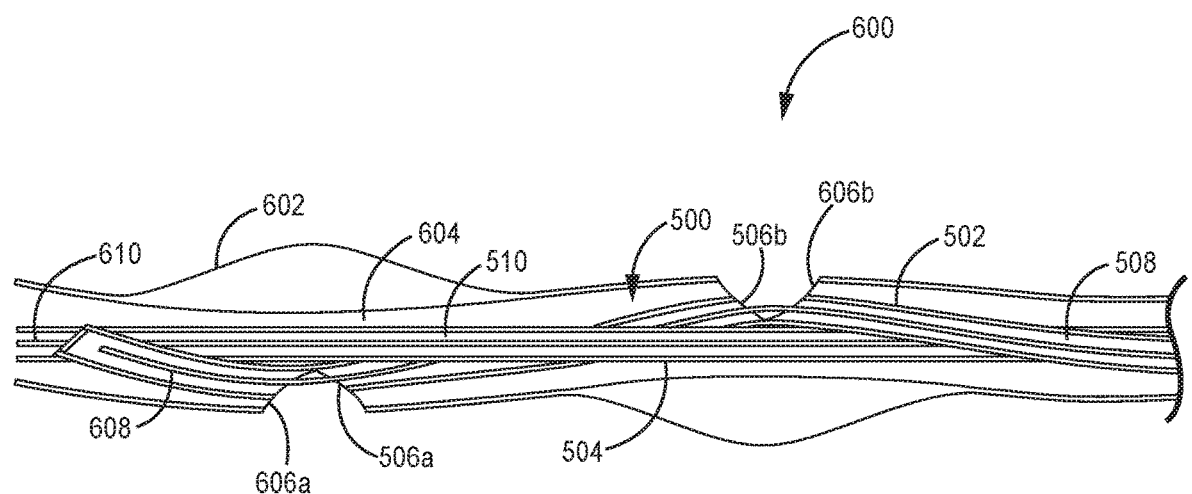
FIG. 6 illustrates a side cross-sectional view of a portion of an example kit for intravascular implantation of an implantable medical device within a patient including the shaft of FIGS. 5A and 5B.

FIG. 6 illustrates a side cross-sectional view of a portion of a kit 600 for intravascular implantation of an implantable medical device (IMD) within a patient including the shaft 500 of FIGS. 5A and 5B. In addition to the shaft 500, as described with respect to FIGS. 5A and 5B, the kit 600 may include an outer jacket 602 surrounding the shaft 500, providing a smooth outer surface to the kit 600 and/or securing the locking shaft 502 and guidewire shaft 504 together. The jacket 602 may define a lumen 604 configured to receive the shaft 500 and ports 606a and 606b configured to expose the respective ports 506a and 506b of the shaft 500. The kit 600 may further include a locking mandrel 608 received within the locking lumen 508 of the locking shaft 502 and a guidewire 610 received within the guidewire lumen 510 of the guidewire shaft 504.

In some examples, the jacket 602 may comprise a thermoplastic elastomer. The jacket 602 may have decreasing durometer from proximal to distal end to increase the flexibility of the distal portion of the kit 600. In some examples, the locking shaft 502 and/or the guidewire shaft 504 may comprise a thermoplastic elastomer and/or may have decreasing durometer from proximal to distal end to increase the flexibility of the distal portion of the kit 600.

In some examples, ports 606 and 506 may be formed at the same time and after jacket 602 has been placed over shaft 500. For examples, locking shaft 502 and guidewire shaft 504 may be individually formed, locking shaft 502 may be twisted about guidewire shaft 504 and/or bonded to guidewire shaft 504 to form shaft 500, jacket 502 may be placed about shaft 500 and, in some examples, heat shrunk about shaft 500, and ports 606 and 506 may be simultaneously formed in locking shaft 502 and jacket 502. In other examples, ports 506 may be formed in locking shaft 502 before jacket 500 is placed over shaft 500.

In some examples, the locking mandrel 608 may include or be coupled to a handle mechanism to allow for a practitioner to manipulate the locking mandrel 608 including, for example, advancing the locking mandrel 608 with respect to the shaft 500 and through the loops of a fixation assembly of an IMD to secure the IMD to the shaft 500 or to retract the locking mandrel 608 with respect to the shaft 500 to release the loops of the fixation assembly and release the IMD from the shaft 500. The handle may comprise an injection molded polymer and may include locking and unlocking functions to lock the locking mandrel 608 in place and release the locking mandrel for movement by the practitioner, respectively. The handle may comprise a male luer threadably fixed to a proximal end of the shaft 500, which may facilitate delivery of the kit via an over the wire method and/or a saline flush prior to introducing the kit into the vasculature.

In some examples, the locking mandrel 608 may comprise stainless steel and/or another suitable metal and/or a thin solid polymer extrusion. In some examples, the locking mandrel 608 may have an outer diameter of approximately 0.2-0.25 mm.

Figure 7:
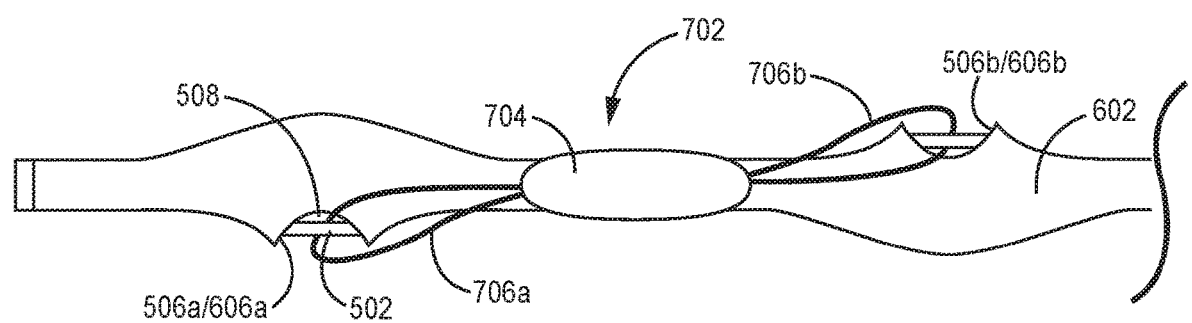
FIG. 7 illustrates a side profile view of a portion of the example kit of FIG. 6 and further including an implantable medical device.

FIG. 7 illustrates a side profile view of a portion of the example kit 600 of FIG. 6 and further including an implantable medical device (IMD) 702. The IMD 702 may be, for example, a sensor assembly, such as the sensor assemblies of FIGS. 1A-2B. IMD 702 may include a housing 704 and a fixation assembly 706 including fixation members 706a and 706b, each forming a loop.

The locking mandrel 502 may be configured to be positioned within the locking lumen 508 and may be configured to pass through one or more of the loops of the fixation assembly 706 of the IMD 702 within the lumen 508 at the respective port 506a and/or 506b to secure the IMD 702 to the shaft 500.

The proximal port 506b may be circumferentially spaced approximately 175-185 degrees about the shaft 500 from the distal port 506a. The circumferential spacing of ports 506 may allow for the IMD 702 to be more tightly secured to the shaft 500, e.g., by providing a greater linear distance between the ports 506, which may reduce the overall profile of the kit 600. In addition, the circumferential spacing of the ports 506 may reduce strain on the fixation members 706a and 706b of the IMD 702.

Twisting of the locking shaft 502 about the guidewire shaft 504, as well as the circumferential spacing of the ports 506, may allow the IMD 702 to be located at a low profile portion of the shaft 500 and jacket 602 such that the overall profile of the kit, including the IMD 702, may be reduced.

Additionally, twisting of the locking shaft 502 about the guidewire shaft 504, as well as the varying thickness of the jacket 602, may provide a predictable bending point and direction, which may improve trackability. For example, portions of the jacket 602 proximate the ports 506a/606a and 506b/606b, may be thicker than at the portion of the jacket 602 between the ports 506a/606a and 506b/606b and adjacent the IMD 702 such that the kit 600 may be less likely to bend at points proximate the ports 506a/606a and 506b/606b at more likely to bend at points between the ports 506a/606a and 506b/606b and adjacent the IMD 702. Additionally, the twisting of the locking shaft 502 about the guidewire shaft 504 may bias the kit 600 to bend about a single axis. For example, the kit 600 may be biased to bend about the axis labeled "x" in FIG. 5A because the locking shaft 502 and guidewire shaft 504 will sit adjacent to one another along that axis such that the kit 600 may be wider along that axis than along any other direction. Additionally, because the jacket 602 may be thinnest at that point, the kit 600 may be biased to bend at that point. The resulting predictable bending point and direction may provide improved trackability.

In some examples, the kit 600 may comprise one or more marker bands, e.g., similar to the marker band 316 shown in FIG. 3A, at a distal portion of the kit 600 which may, comprise, for example, a gold radiopaque ribbon section, a barium sulphate filled thermoplastic elastomer extrusion, and/or a tungsten marker band and may assist a practitioner in visualizing the end of the kit 600. The marker band may comprise, for example, approximately 60% barium sulphate. One or more marker bands may be, for example, at a distal end of the kit 600, proximate one or more of the ports 506, proximate a portion of the jacket 602 configured to be adjacent to the IMD 702 when the IMD 702 is secured to the kit 600, and/or any other suitable location as may assist a clinician in visualizing and positioning the kit 600 and implanting the IMD 702 within the vasculature of a patient.

Figure 8A:
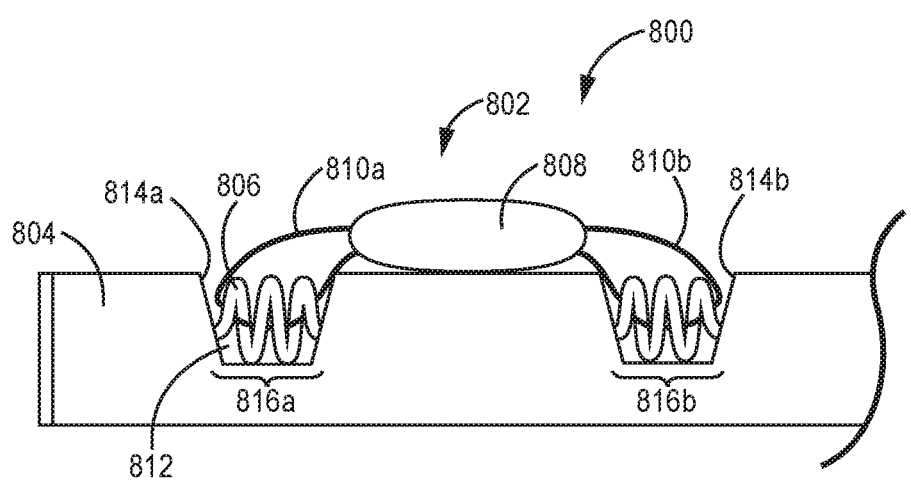
FIGS. 8A and 8B illustrate side profile and side cross-sectional views of a portion of another example kit for intravascular implantation of an implantable medical device within a patient.
Figure 8B:
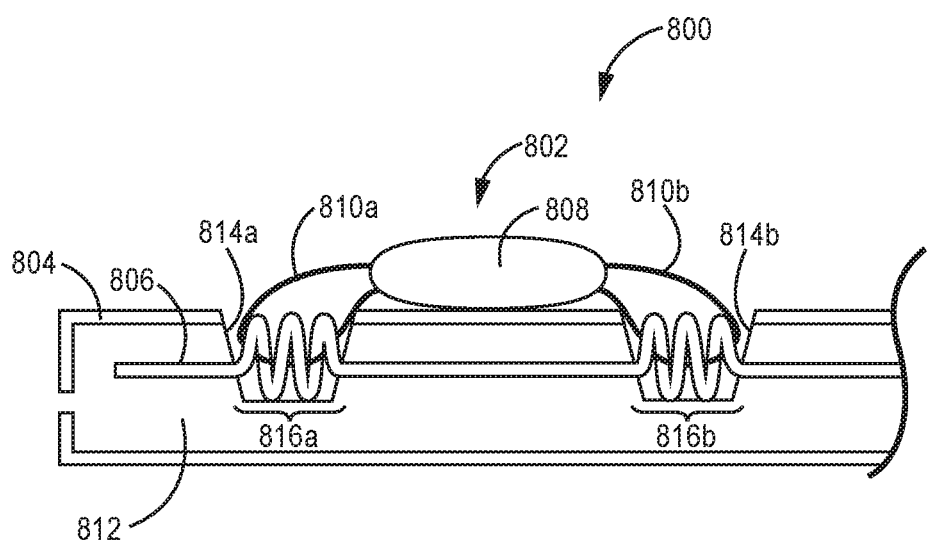

FIGS. 8A and 8B illustrate side profile and side cross-sectional views of a portion of another example kit 800 for intravascular implantation of an implantable medical device (IMD) 802 within a patient. The IMD 802 may be, for example, a sensor assembly, such as the sensor assemblies 114, 10, 11*a*, and 11*b* of FIGS. 1A-2B. The kit 800 may include an elongated shaft 804 and a locking mandrel 806. In some examples, the kit 800 may further include the IMD 802. The IMD 802 may include a housing 808 and a fixation assembly 810. The fixation assembly 810 may include, for example, two fixation members 810*a* and 810*b* which may each form a loop.

The shaft 804 may be sized to traverse a vasculature of a patient. The elongated shaft 804 may define a longitudinal lumen 812 and one or more ports 814 in fluid communication with the lumen 812. Although the lumen 812 is shown as being a single lumen, the lumen 812 as described herein may refer to any suitable number of lumens 812. Each of the ports 814*a* and 814*b* may be sized to receive at least a portion of a respective loop of the fixation assembly 810 of the IMD 802. The ports 814 may include a proximal port 814*b* and a distal port 814*a*, each defined on a side wall of the elongated shaft elongated shaft 804.

The locking mandrel 806 may be configured to be positioned within the lumen 812 of the shaft 804 and may be configured to pass through one or more of the loops of the fixation assembly 810 of the IMD 802 within the lumen 812 at the respective port 814*a* and/or 814*b* to secure the IMD 802 to the shaft 804. More specifically, the locking mandrel 806 may include at least one helical portion 816*a* or 816*b* and the locking mandrel 806 may be configured to be rotated with respect to the shaft 804 to pass through the respective loop of the fixation assembly 810. The locking mandrel 806 may also be configured to be rotated in an opposite direction with respect to the shaft 804 to release the respective loop of the fixation assembly 810 and thus release the IMD 802 from the shaft 804. These features may allow for the loops of the fixation assembly 810 to be released at the same time instead of in sequence.

In some examples, the kit 800 may additionally include a guidewire. The locking mandrel 806 may define a guidewire lumen configured for passage of the guidewire. In some examples, the lumen 812 may be configured such that the guidewire and the locking mandrel 806 may be positioned adjacent to one another within the lumen 812.

In some examples, the shaft 804 may be a braided stainless steel wire shaft. In some examples, the shaft 804 may include a jacket comprising a thermoplastic elastomer. The jacket may have decreasing durometer from proximal to distal end to increase the flexibility of the distal portion of the shaft 804. The outer diameter of the shaft 804 may be approximately 2-2.6 mm and in inner diameter of the shaft 804 may be approximately 1.8-2 mm.

In some examples, the ports 814 may be positioned in a distal portion of the shaft 804 that is approximately 75-80 mm long and may be spaced approximately 55-57 mm apart. In some examples, a distal portion of the shaft 804 including the ports 814 may comprise a single polymer extrusion and may not be braided.

In some examples, the locking mandrel 806 may include or be coupled to a handle mechanism to allow for a practitioner to manipulate the locking mandrel 806 including, for example, rotating the locking mandrel 806 with respect to the shaft 804 and through the loops of the fixation assembly 810 to secure the IMD 802 to the shaft 804 or to rotate the locking mandrel 806 in the opposite direction with respect to the shaft 804 to release the loops of the fixation assembly 810 and release the IMD 802 from the shaft 804. For example, the handle may include a turn wheel to torque the locking mandrel 806. The handle may comprise an injection molded polymer and may include locking and unlocking functions to lock the locking mandrel 806 in place and release the locking mandrel 806 for movement by the practitioner, respectively. The handle may comprise a male luer threadably fixed to a proximal end of the shaft 804, which may facilitate delivery of the kit 800 via an over the wire method and/or a saline flush prior to introducing the kit 800 into the vasculature.

In some examples, the locking mandrel 806 may run the full length of the shaft 804. In some examples, the locking mandrel 306 may have an outer diameter of approximately 0.2-0.25 mm. The locking mandrel 806 may contain one or more helical or hooked portions, such as the helical portions 816. These portions may include preformed corkscrew or hooked features that line up with the ports 814 at the distal end of the shaft 804.

In some examples, the shaft 804 may comprise one or more marker bands, e.g., similar to the marker band 316 shown in FIG. 3A, at a distal portion of the shaft 804 which may, comprise, for example, a gold radiopaque ribbon section, a barium sulphate filled thermoplastic elastomer extrusion, and/or a tungsten marker band and may assist a practitioner in visualizing the end of the shaft 804. The marker band may comprise, for example, approximately 60% barium sulphate. One or more marker bands may be, for example, at a distal end of the shaft 804, proximate one or more of the ports 814, proximate a portion of the shaft 804 configured to be adjacent to the IMD 802 when the IMD 802 is secured to the shaft 804, and/or any other suitable location as may assist a clinician in visualizing and positioning the kit 800 and implanting the IMD 802 within the vasculature of a patient.

Features of the different examples described herein may be used in any suitable combination. For example, a helical locking mandrel, as illustrated and described with respect to FIGS. 8A and 8B, may be used in combination with circumferentially spaced ports, as illustrated and described with respect to FIG. 4, a multi-lumen shaft, as illustrated and described with respect to FIGS. 5A-7, and/or any other feature described herein, according to particular needs.

Figure 9:
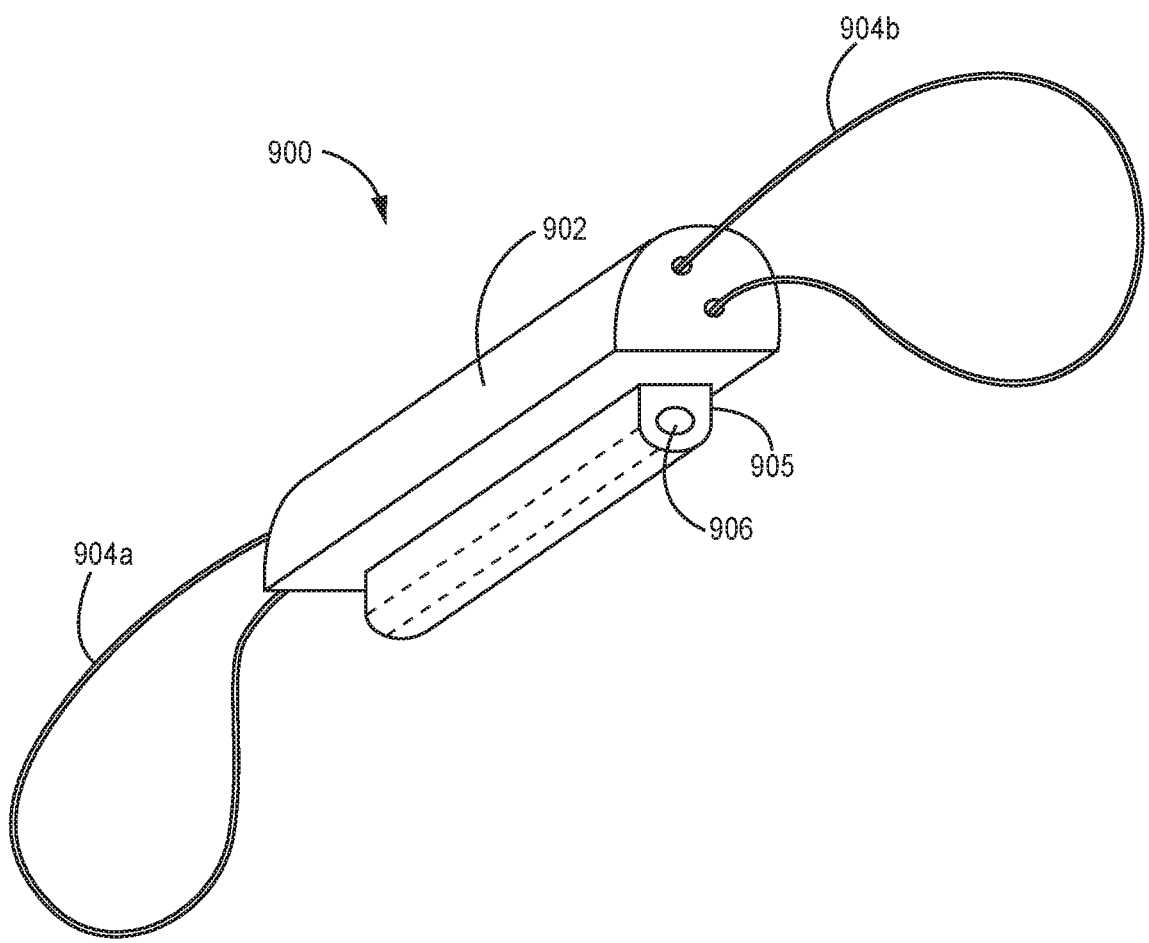
FIG. 9 illustrates a perspective view of another example of an implantable medical device.

FIG. 9 illustrates a perspective view of another example of an implantable medical device (IMD) 900. The IMD 900 may be, for example, a sensor assembly, such as the sensor assemblies 114, 10, 11a, and 11b of FIGS. 1A-2B.

The IMD 900 may include a housing 902 and a fixation assembly 904. The fixation assembly 904 may include, for example, two fixation members 904a and 904b which may each form a loop. The housing 902 may define a lumen 906. In the illustrated example, housing 902 includes a locking protrusion 905 from a surface of the housing that defines the lumen 906. In the illustrated example, the surface from which protrusion 905 protrudes is a bottom surface of housing 902 configured to be most proximate to an elongated shaft of a kit for implanting the IMD 900.

Figure 10A:
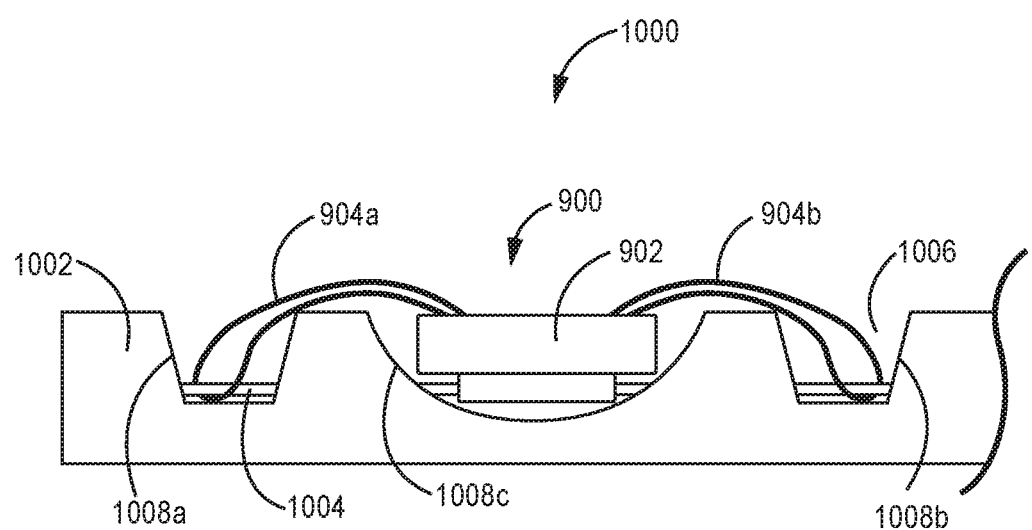
FIGS. 10A and 10B illustrate side profile and side cross-sectional views of a portion of an example kit for intravascular implantation of the implantable medical device of FIG. 9 within a patient.
Figure 10B:
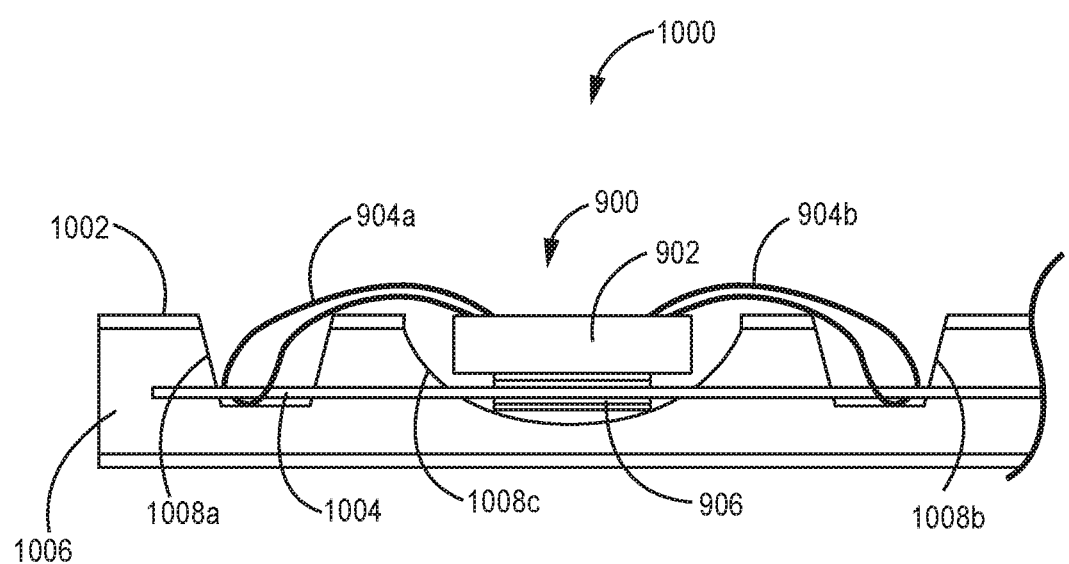

FIGS. 10A and 10B illustrate side profile and side cross-sectional views of a portion of an example kit 1000 for intravascular implantation of the implantable medical device (IMD) 900 of FIG. 9 within a patient. The kit 1000 may include an elongated shaft 1002 and a locking mandrel 1004. In some examples, the kit 1000 may further include the IMD 900. The shaft 1002 may be sized to traverse a vasculature of a patient. The elongated shaft 1002 may define a longitudinal lumen 1006 and one or more ports 1008 in fluid communication with the lumen 1006. Although the lumen 1006 is shown as being a single lumen, the lumen 1006 as described herein may refer to any suitable number of lumens 1006.

Each of the ports 1008a and 1008b may be sized to receive at least a portion of a respective loop of the fixation assembly 904 of the IMD 900. In addition, port 1008c may be sized to receive at least a portion of the housing 902 of the implantable medical device 900. The ports 1008 may include a proximal port 1008b, a distal port 1008a, and a middle port 1008c, each defined on a side wall of the elongated shaft elongated shaft 1002.

The locking mandrel 1004 may be configured to be positioned within the lumen 1006 of the shaft 1002 and may be configured to pass through one or more of the loops of the fixation assembly 904 of the IMD 900 within the lumen 1006 at the respective port 1008a and/or 1008b to secure the IMD 900 to the shaft 1002. In addition, the locking mandrel 1004 may be configured to pass through the lumen 906 defined by the housing 902 of the implantable medical device 900 at the port 1008c.

In some examples, the locking mandrel 1004 may comprise a braided shaft. In some examples, the locking mandrel 1004 may comprise a polymer extrusion. In some examples, the locking mandrel 1004 may have an outer diameter of approximately 0.17-0.25 mm and may be configured to run alongside a guidewire in the lumen 1006. In some examples, the locking mandrel 1004 may have an outer diameter of approximately 0.8-0.9 mm and an inner diameter of approximately 0.6-0.65 mm may be configured to receive a guidewire.

Having the port 1008c sized to receive at least a portion of the housing 902 of the implantable medical device 900 and having the locking mandrel 1004 configured to pass through the lumen 906 defined by the housing 902 of the implantable medical device 900 at the port 1008c may allow the IMD 900 to be more securely positioned on the shaft 1002 and may additional allow the kit 1000 to have a reduced profile.

In some examples, the proximal port 1008b may be circumferentially spaced approximately 175-185 degrees about the shaft 1002 from the distal port 1008a. The circumferential spacing of ports 1008 may allow for the IMD 900 to be more tightly secured to the shaft 1002, e.g., by providing a greater linear distance between the ports 1008, which may reduce the overall profile of the kit 1000.

In addition, the circumferential spacing of the ports 1008 may reduce strain on the fixation members 904a and 904b of the IMD 900.

In some examples, the locking mandrel 1004 may include at least one helical portion and may be configured to be rotated with respect to the shaft 1002 to pass through the respective loop of the fixation assembly 904 and/or a lumen defined by the IMD housing 902. The locking mandrel 1004 may also be configured to be rotated in an opposite direction with respect to the shaft 1002 to release the respective loop of the fixation assembly 904 and/or the IMD housing 902 and thus release the IMD 900 from the shaft 1002. In such an example, the IMD housing 902 may define a lumen that runs perpendicular to the view shown in FIGS. 10A and 10B.

In some examples, the shaft 1002 may be a braided stainless steel wire shaft. In some examples, the shaft 1002 may include a jacket comprising a thermoplastic elastomer. The jacket may have decreasing durometer from proximal to distal end to increase the flexibility of the distal portion of the shaft 1002. The outer diameter of the shaft 1002 may be approximately 2-2.6 mm and the inner diameter of the shaft 1002 may be approximately 1.8-2 mm. In some examples, the ports 1008 may be positioned in a distal portion of the shaft 1002 that is approximately 75-80 mm long.

In some examples, the locking mandrel 1004 may include or be coupled to a handle mechanism to allow for a practitioner to manipulate the locking mandrel 1004 including, for example, advancing the locking mandrel 1004 with respect to the shaft 1002 and through the loops of the fixation assembly 904 and the lumen 906 of the housing 902 the IMD 900 to secure the IMD 900 to the shaft 1002 or to retract the locking mandrel 1004 with respect to the shaft 1002 to release the loops of the fixation assembly 904 the housing 902 and release the IMD 900 from the shaft 1002. The handle may comprise an injection molded polymer and may include locking and unlocking functions to lock the locking mandrel 1004 in place and release the locking mandrel 1004 for movement by the practitioner, respectively. The handle may comprise a male luer threadably fixed to a proximal end of the shaft 1002, which may facilitate delivery of the kit 1000 via an over the wire method and/or a saline flush prior to introducing the kit 1000 into the vasculature.

In some examples, the locking mandrel 1004 may be a braided shaft. In some examples, the locking mandrel 1004 may have an outer diameter of approximately 0.17-0.25 mm and may be configured to run alongside a guidewire in the lumen 1006. In some examples, the locking mandrel 1004 may have an outer diameter of approximately 0.8-0.9 mm and an inner diameter of approximately 0.6-0.65 mm may be configured to receive a guidewire.

In some examples, the shaft 1002 may comprise a marker band at a distal portion of the shaft 1002 which may, comprise, for example, a gold radiopaque ribbon section, a barium sulphate filled thermoplastic elastomer extrusion, and/or a tungsten marker band and may assist a practitioner in visualizing the end of the shaft 1002. The marker band may comprise, for example, approximately 60% barium sulphate. In some examples, the shaft 1002 may comprise one or more marker bands, e.g., similar to the marker band 316 shown in FIG. 3A, at a distal portion of the shaft 1002 which may, comprise, for example, a gold radiopaque ribbon section, a barium sulphate filled thermoplastic elastomer extrusion, and/or a tungsten marker band and may assist a practitioner in visualizing the end of the shaft 1002. The marker band may comprise, for example, approximately 60% barium sulphate. One or more marker bands may be, for example, at a distal end of the shaft 1002, proximate one or more of the ports 1008, proximate a portion of the shaft 1002 configured to be adjacent to the IMD 900 when the IMD 900 is secured to the shaft 1002, and/or any other suitable location as may assist a clinician in visualizing and positioning the kit 1000 and implanting the IMD 900 within the vasculature of a patient.

Features of the different examples described herein may be used in any suitable combination. For example, a shaft with a port to receive at least a portion of an IMD, as illustrated and described with respect to FIGS. 10A and 10B, may be used in combination with circumferentially spaced ports, as illustrated and described with respect to FIG. 4, a multi-lumen shaft, as illustrated and described with respect to FIGS. 5A-7, a helical locking mandrel, as illustrated and described with respect to FIGS. 8A and 8B, and/or any other feature described herein, according to particular needs.

Figure 11:
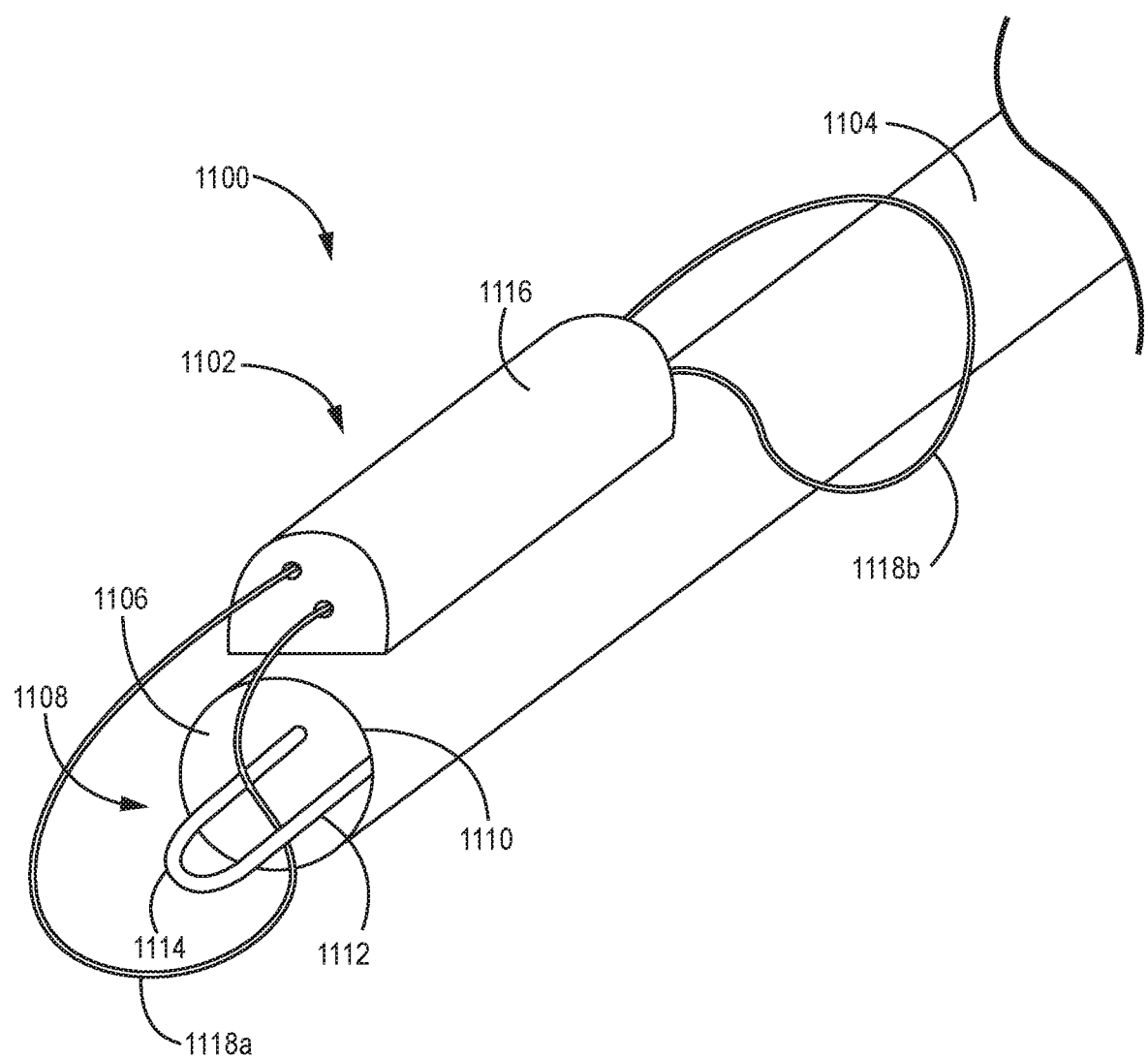
FIG. 11 illustrates a perspective view of a portion of another example kit for intravascular implantation of an implantable medical device within a patient.

FIG. 11 illustrates a perspective view of a portion of another example kit 1100 for intravascular implantation of an implantable medical device (IMD) 1102 within a patient.

The IMD 1102 may be, for example, a sensor assembly, such as the sensor assemblies 114, 10, 11a, and 11b of FIGS. 1A-2B. The IMD 1102 may include a housing 1116 and a fixation assembly 1118. The fixation assembly 1118 may include, for example, two fixation members 1118a and 1118b which may each form a loop.

The kit 1100 may include an elongated shaft 1004, sized to traverse a vasculature of the patient, and a locking mandrel 1112. In some examples, the kit 1000 may further include the IMD 1102. The shaft may define at least one longitudinal lumen 1006 and a distal opening 1008 of lumen 1006 at a distal end 1110 of the shaft 1104. The locking mandrel 1112 may be configured to be positioned within the lumen 1106 of the shaft 1104 and may define a hook 1114 configured to pass through a loop of the fixation assembly 1118 of the IMD 1102 proximate the distal opening 1108.

The locking mandrel 112 may be configured to be advanced with respect to the shaft 1104 to release the IMD 1102 from the shaft 1104. For example, advancing the locking mandrel 112 with respect to the shaft 1104 may allow the loop of the fixation assembly 1118 to be released from the hook 114 and therefore be released from the shaft 1104.

In some examples, the shaft 1004 may be a braided stainless steel wire shaft. In some examples, the shaft 1004 may include a jacket comprising a thermoplastic elastomer. The jacket may have decreasing durometer from proximal to distal end to increase the flexibility of the distal portion of the shaft 1004. The outer diameter of the shaft 1004 may be approximately 2-2.6 mm and the inner diameter of the shaft 1004 may be approximately 1.5-2 mm.

In some examples, the locking mandrel 1112 may include or be coupled to a handle mechanism to allow for a practitioner to manipulate the locking mandrel 1112 including, for example, advancing and retracting the locking mandrel 1112 with respect to the shaft 1004 to place the hook 1114 through a loops of the fixation assembly 1118 to secure the IMD 1002 to the shaft 1004 or to advance the locking mandrel 1112 with respect to the shaft 1004 to release the loop of the fixation assembly 1118 and release the IMD 1002 from the shaft 1004. The handle may comprise an injection molded polymer and may include locking and unlocking functions to lock the locking mandrel 1112 in place and release the locking mandrel for movement by the practitioner, respectively. The handle may comprise a male luer threadably fixed to a proximal end of the shaft 1004, which may facilitate delivery of the kit 1100 via an over the wire method and/or a saline flush prior to introducing the kit 1100 into the vasculature.

In some examples, the locking mandrel 1112 may, but does not necessarily run the full length of the shaft 1004. In some examples, the locking mandrel 1112 may have an outer diameter of approximately 0.2-0.25 mm.

In some examples, the shaft 1000 may comprise one or more marker bands, e.g., similar to the marker band 316 shown in FIG. 3A, at a distal portion of the shaft 1000 which may, comprise, for example, a gold radiopaque ribbon section, a barium sulphate filled thermoplastic elastomer extrusion, and/or a tungsten marker band and may assist a practitioner in visualizing the end of the shaft 1000. The marker band may comprise, for example, approximately 60% barium sulphate. One or more marker bands may be, for example, at a distal end of the shaft 1000, proximate a portion of the shaft 1000 configured to be adjacent to the IMD 1102 when the IMD 1102 is secured to the shaft 1000, and/or any other suitable location as may assist a clinician in visualizing and positioning the kit 1100 and implanting the IMD 1102 within the vasculature of a patient.

Features of the different examples described herein may be used in any suitable combination. For example, a shaft with a distal opening at a distal end and a locking mandrel configured to pass through a loop of an IMD proximate the distal opening, as illustrated and described with respect to FIG. 11, may be used in combination with a multi-lumen shaft, as illustrated and described with respect to FIGS. 5A-7, a helical locking mandrel, as illustrated and described with respect to FIGS. 8A and 8B (e.g., a helical portion may be used in place of the hooked portion of the locking mandrel and the hooked portion may be rotated to engage or disengage with the loop of the IMD, a shaft with a port to receive at least a portion of an IMD, as illustrated and described with respect to FIGS. 10A and 10B, and/or any other feature described herein, according to particular needs.

FIG. 12 illustrates a side view of a portion of another example kit 1200 for intravascular implantation of an implantable medical device (IMD) 1202 within a patient. The kit 1200 may be similar to that of FIGS. 3A and 3B and may include an elongated shaft 1204, defining a lumen 1206, a distal port 1208a, and a proximal port 1208b. The shaft 1204 may be sized to traverse a vasculature of a patient. The kit 1200 may also include a locking mandrel 1210, and an IMD 1202, including a housing 1212 and a fixation assembly 1214 including fixation members 1214a and 1214b, each forming a loop. The IMD 1202 may be, for example, a sensor assembly, such as the sensor assemblies 114, 10, 11a, 11b of FIGS. 1A-2B.

The locking mandrel 1210 may be configured to be positioned within the lumen 1206 of the shaft 1204 and may be configured to pass through one or more of the loops of the fixation assembly 1214 of the IMD 1202 within the lumen 1206 at the respective port 1208a and/or 1208b to secure the IMD 1202 to the shaft 1204.

In some examples, the locking mandrel 1210 may comprise a braided shaft. In some examples, the locking mandrel 1210 may comprise a polymer extrusion. In some examples, the locking mandrel 1210 may have an outer diameter of approximately 0.17-0.25 mm and may be configured to run alongside a guidewire in the lumen 1206. In some examples, the locking mandrel 1210 may have an outer diameter of approximately 0.8-0.9 mm and an inner diameter of approximately 0.6-0.65 mm may be configured to receive a guidewire.

The shaft 1204 may include a reduced profile portion 1216 that defines a reduced profile with respect to one or more other portions of the shaft. At least a portion of the reduced profile portion 1216 may be configured to be adjacent to the IMD 1202 when the implantable medical device 1202 is positioned on the shaft. This may allow for the kit 1200 to have an overall reduced profile, which may improve navigation through the vasculature. This may also allow the IMD 1202 to be more securely positioned on the shaft 1204.

In some examples, the kit 1200 may additionally include a guidewire. The locking mandrel 1210 may define a guidewire lumen configured for passage of the guidewire. In some examples, the lumen 1204 may be configured such that the guidewire and the locking mandrel 1210 may be positioned adjacent to one another within the lumen 1204.

In some examples, the proximal port 1208*b* may be circumferentially spaced approximately 175-185 degrees about the shaft 1204 from the distal port 1208*a*. The circumferential spacing of ports 1208 may allow for the IMD 1202 to be more tightly secured to the shaft 1204, e.g., by providing a greater linear distance between the ports 1208, which may reduce the overall profile of the kit 1200. In addition, the circumferential spacing of the ports 1208 may reduce strain on the fixation members 1214*a* and 1214*b* of the IMD 1202.

In some examples, the locking mandrel 1210 may include at least one helical portion and may be configured to be rotated with respect to the shaft 1204 to pass through the respective loop of the fixation assembly 1214 and/or a lumen defined by the IMD housing 1212. The locking mandrel 1210 may also be configured to be rotated in an opposite direction with respect to the shaft 1204 to release the respective loop of the fixation assembly 1214 and/or the IMD housing 1212 and thus release the IMD 1202 from the shaft 1204. In such an example, the IMD housing 1212 may define a lumen that runs perpendicular to the view shown in FIG. 12.

In some examples, the shaft 1204 may be a braided stainless steel wire shaft. In some examples, the shaft 1204 may include a jacket comprising a thermoplastic elastomer. The jacket may have decreasing durometer from proximal to distal end to increase the flexibility of the distal portion of the shaft 1204.

The outer diameter of the shaft 1204 may be approximately 2-2.6 mm and an inner diameter of the shaft 1204 may be approximately 1.7-2.3 mm. The reduced profile portion 1216 may have an outer diameter of approximately 1.0-1.2 mm.

In some examples, the ports 1208 may be positioned in a polymer distal portion of the shaft 1204 that is approximately 75-80 mm long and the ports 1208 may be approximately 55-57 mm apart. A distal polymer portion of the shaft 1204 may be bonded (e.g., by glue such as cyanoacrylate, ultraviolet cured, or similar glue) to a distal end of a proximal portion of the shaft 1204. The proximal portion of the shaft 1204 may be, for example, constructed of SS304 or a similar, braided polymer (pebax7233/Polyamide).

In some examples, the locking mandrel 1210 may include or be coupled to a handle mechanism to allow for a practitioner to manipulate the locking mandrel 1210 including, for example, advancing the locking mandrel 1210 with respect to the shaft 1204 and through the loops of the fixation assembly 1214 to secure the IMD 1202 to the shaft 1204 or to retract the locking mandrel 1210 with respect to the shaft 1204 to release the loops of the fixation assembly 1214 and release the IMD 1202 from the shaft 1204. The handle may comprise an injection molded polymer and may include locking and unlocking functions to lock the locking mandrel 1210 in place and release the locking mandrel 1210 for movement by the practitioner, respectively. The handle may comprise a male luer threadably fixed to a proximal end of the shaft 1204, which may facilitate delivery of the kit 1200 via an over the wire method and/or a saline flush prior to introducing the kit 1200 into the vasculature.

In some examples, the locking mandrel 1210 may be a braided shaft. In some examples, the locking mandrel 1210 may have an outer diameter of approximately 0.8-0.9 mm and an inner diameter of approximately 0.6-0.65 mm. In some examples, the locking mandrel 1210 may be configured to receive a guidewire, e.g., may define a lumen there through.

In some examples, the shaft 1204 may comprise one or more marker bands, e.g., similar to the marker band 316 shown in FIG. 3A, at a distal portion of the shaft 1204 which may, comprise, for example, a gold radiopaque ribbon section, a barium sulphate filled thermoplastic elastomer extrusion, and/or a tungsten marker band and may assist a practitioner in visualizing the end of the shaft 1204. The marker band may comprise, for example, approximately 60% barium sulphate. One or more marker bands may be, for example, at a distal end of the shaft 1204, proximate one or more of the ports 1208, proximate a portion of the shaft 1204 configured to be adjacent to the IMD 1202 when the IMD 1202 is secured to the shaft 1204, and/or any other suitable location as may assist a clinician in visualizing and positioning the kit 1200 and implanting the IMD 1202 within the vasculature of a patient.

Features of the different examples described herein may be used in any suitable combination. For example, a shaft with a reduced portion configured to be adjacent an IMD when the IMD is secured to the shaft, as illustrated and described with respect to FIG. 12, may be used in combination with circumferentially spaced ports, as illustrated and described with respect to FIG. 4, a multi-lumen shaft, as illustrated and described with respect to FIGS. 5A-7, a helical locking mandrel, as illustrated and described with respect to FIGS. 8A and 8B, a shaft with a port to receive at least a portion of an IMD, as illustrated and described with respect to FIGS. 10A and 10B, a shaft with a distal opening at a distal end and a locking mandrel configured to pass through a loop of an IMD proximate the distal opening, as illustrated and described with respect to FIG. 11, and/or any other feature described herein, according to particular needs.

Figure 13A:
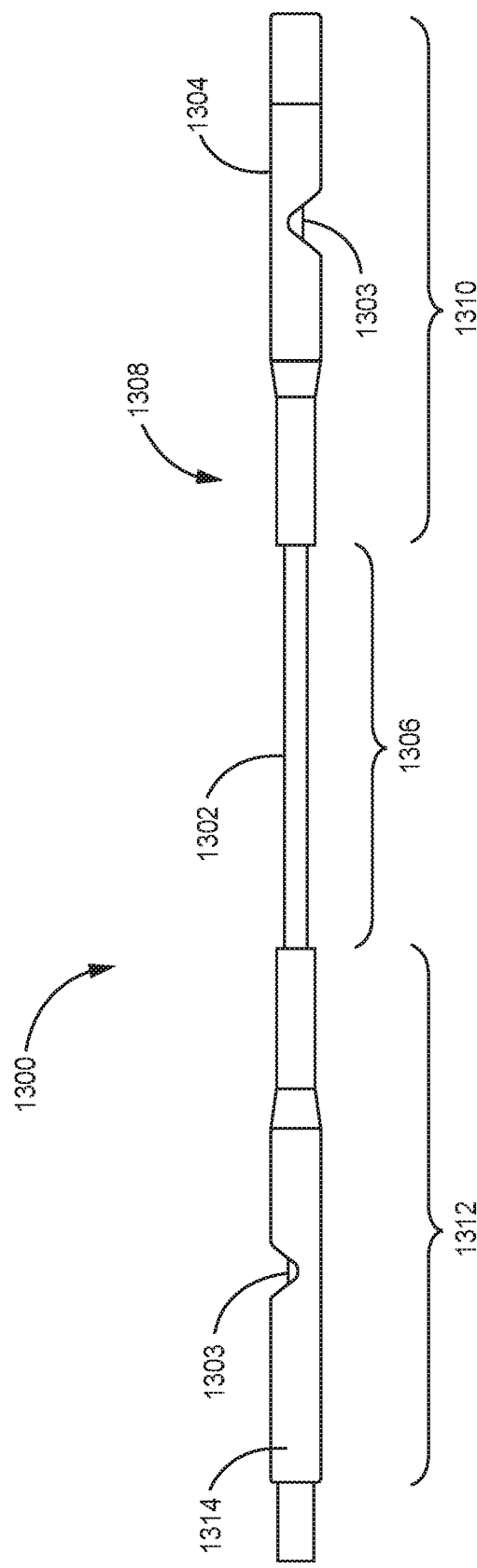
FIGS. 13A and 13B illustrate side profile and cross-sectional views of a portion of another example kit for intravascular implantation of an implantable medical device within a patient.
Figure 13B:
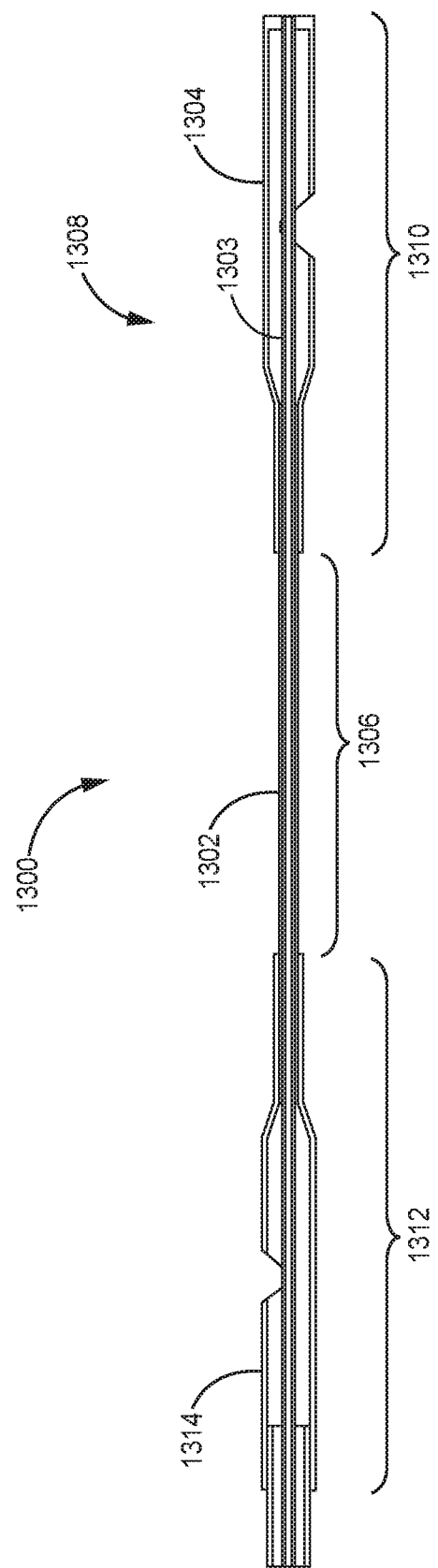

FIGS. 13A and 13B illustrate side profile and cross-sectional views of a portion of another example kit 1300 for intravascular implantation of an implantable medical device (IMD) within a patient. The kit 1300 may be similar to the kit 1200 of FIG. 12, including an elongated shaft 1308 with a reduced profile portion 1306, allowing for improved navigation through the vasculature. In addition to the reduced profile portion 1306, the shaft 1308 may include a proximal portion 1312 proximal to the reduced profile portion 1306 and a distal portion 1310 distal to the reduced profile portion 1306. Each of the reduced profile portion 1306, the proximal portion 1312, and the distal portion 1310 may be configured to receive a respective portion of a locking mandrel 1303. In addition, the proximal portion 1312 may include a proximal outer shaft 1314 configured to surround at least a first portion of the locking mandrel 1303 and the distal portion 1310 may include a distal outer shaft 1304 configured to surround at least a second portion of the locking mandrel 1302.

As shown and described with respect to FIGS. 12-13B, an elongated shaft with a reduced profile portion for improved navigation through the vasculature may be formed monolithically, as shown and described with respect to FIG. 12, or by multiple components, as described with respect to FIGS. 13A and 13B.

In some examples, the proximal outer shaft 1314 may be glued or thermally bonded to at least a first portion of a middle outer shaft 1302 and the distal outer shaft 1304 may be glued or thermally bonded to at least the second portion of the middle outer shaft 1302 such that the middle outer shaft connects the proximal outer shaft 1314 and the distal outer shaft 1304. Each of the proximal outer shaft 1314 and the distal outer shaft 1304 may be polymer tapered tube.

In some examples, the locking mandrel 1303 may be a braided stainless steel wire shaft. The outer diameter of the locking mandrel 1303 may be approximately 1-1.15 mm.

In some examples, shaft 1308 may include a jacket comprising a thermoplastic elastomer. The jacket may have decreasing durometer from proximal to distal end to increase the flexibility of the distal portion of the shaft 1308. The outer diameter of the shaft 1308 may be approximately 2.1-2.6 mm and an inner diameter of the shaft 1308 may be approximately 1.7-2.3 mm.

In some examples, the locking mandrel 1303 may include or be coupled to a handle mechanism to allow for a practitioner to manipulate the locking mandrel 1303 including, for example, advancing the locking mandrel 1303 with respect to the shaft 1308 and through loops of a fixation assembly to secure an IMD to the shaft 1308 or to retract the locking mandrel 1303 with respect to the shaft 1308 to release the loops of the fixation assembly and release the IMD from the shaft 1308. The handle may comprise an injection molded polymer and may include locking and unlocking functions to lock the locking mandrel 1303 in place and release the locking mandrel 1303 for movement by the practitioner, respectively. The handle may comprise a male luer threadably fixed to a proximal end of the shaft 1308, which may facilitate delivery of the kit via an over the wire method and/or a saline flush prior to introducing the kit into the vasculature.

In some examples, the kit 1300 may additionally include a guidewire. The locking mandrel 1303 may define a guidewire lumen configured for passage of the guidewire. In some examples, the lumen defined by the proximal outer shaft 1314, middle outer shaft 1302, and distal outer shaft 1304 may be configured such that the guidewire and the locking mandrel 1303 may be positioned adjacent to one another within the lumen.

In some examples, a locking mandrel 1303 may be a braided shaft. In some examples, the locking mandrel 1303 may have an outer diameter of approximately 0.8-0.9 mm and an inner diameter of approximately 0.6-0.65 mm may be configured to receive a guidewire.

In some examples, the shaft 1308 may comprise one or more marker bands, e.g., similar to the marker band 316 shown in FIG. 3A, at a distal portion of the shaft 1308 which may, comprise, for example, a gold radiopaque ribbon section, a barium sulphate filled thermoplastic elastomer extrusion, and/or a tungsten marker band and may assist a practitioner in visualizing the end of the shaft 1308. The marker band may comprise, for example, approximately 60% barium sulphate. One or more marker bands may be, for example, at a distal end of the shaft 1308, proximate one or more of the ports, proximate a portion of the shaft 1308 configured to be adjacent to the IMD 1102 when the IMD 1202 is secured to the shaft 1308, and/or any other suitable location as may assist a clinician in visualizing and positioning the kit 1300 and implanting an IMD within the vasculature of a patient.

Features of the different examples described herein may be used in any suitable combination. For example, a shaft with a reduced portion configured to be adjacent an IMD when the IMD is secured to the shaft, as illustrated and described with respect to FIGS. 13A and 13B, may be used in combination with circumferentially spaced ports, as illustrated and described with respect to FIG. 4, a multi-lumen shaft, as illustrated and described with respect to FIGS. 5A-7, a helical locking mandrel, as illustrated and described with respect to FIGS. 8A and 8B, a shaft with a port to receive at least a portion of an IMD, as illustrated and described with respect to FIGS. 10A and 10B, a shaft with a distal opening at a distal end and a locking mandrel configured to pass through a loop of an IMD proximate the distal opening, as illustrated and described with respect to FIG. 11, and/or any other feature described herein, according to particular needs.

Figure 14:
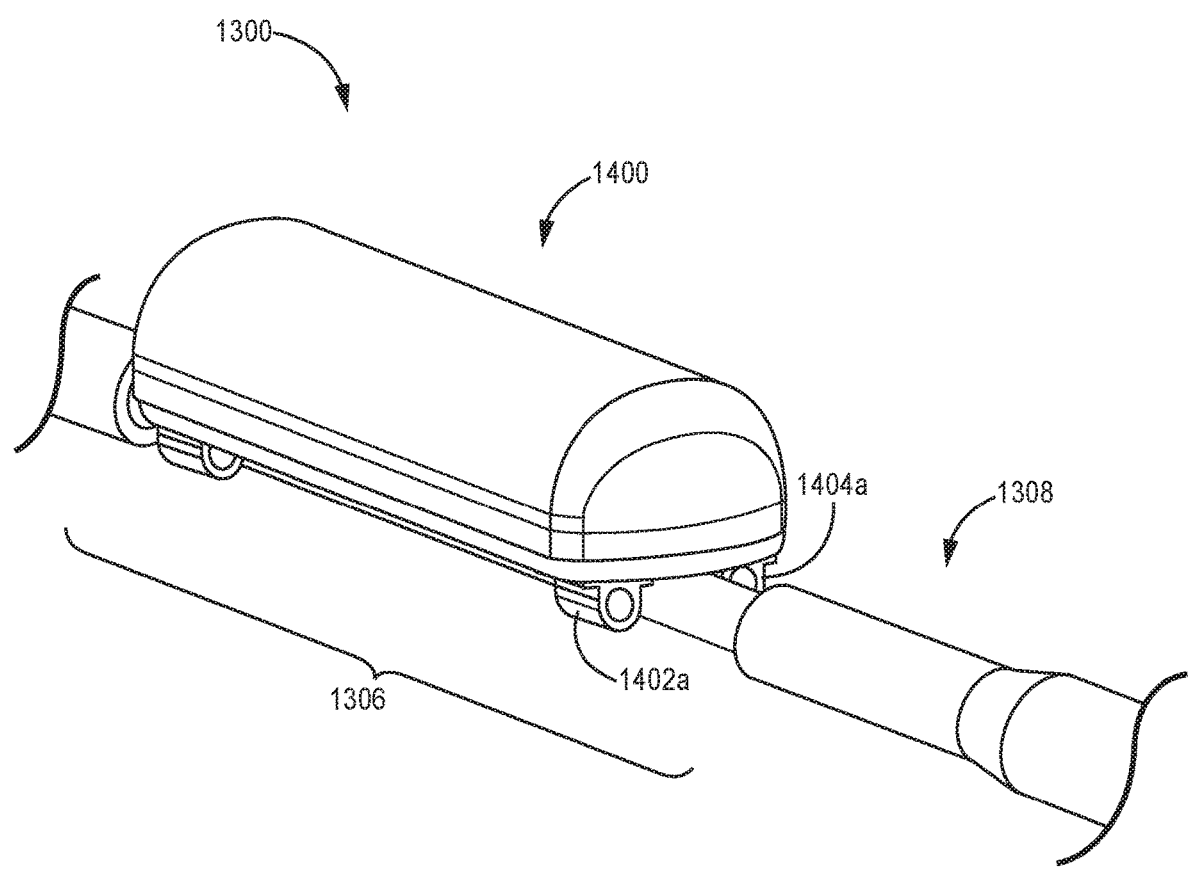
FIG. 14 illustrates a perspective view of a portion of the example kit of FIGS. 13A and 13B and further including an implantable medical device.

FIG. 14 illustrates a perspective view of a portion of the example kit 1300 of FIGS. 13A and 13B and further including an implantable medical device (IMD) 1400. The IMD 1400 may be, for example, a sensor assembly, such as the sensor assemblies 114 and 10 of FIGS. 1A-2B. The IMD 1400 may include two or more cleats 1402a and 1402b and the reduced profile portion 1306 of the shaft 1308 may be configured to be positioned between two cleats 1402a and 1402b of the IMD 1400 when the IMD 1400 is positioned on the shaft 1308. Although not illustrated in FIG. 14, cleats 1402 may be configured to receive fixation loops, e.g., similar to fixation members 30a and 30b of sensor assemblies 11a and 11b of FIGS. 2A and 2B, and thereby connect the fixation members to the housing of IMD 1400. This may allow for the IMD 1400 to be more securely positioned on the shaft 1308, and for the kit 1400 to have a reduced profile, e.g., because the height of the cleats 1402 will not contribute to the profile of the kit 1400, improving navigation of the kit 1400 through the vasculature.

Features of the different examples described herein may be used in any suitable combination. For example, an IMD with cleats configured to be positioned about a shaft when the IMD is secured to the shaft and formed, as illustrated and described with respect to FIG. 14, may be used in combination with circumferentially spaced ports, as illustrated and described with respect to FIG. 4, a multi-lumen shaft, as illustrated and described with respect to FIGS. 5A-7, a helical locking mandrel, as illustrated and described with respect to FIGS. 8A and 8B, a shaft with a port to receive at least a portion of an IMD, as illustrated and described with respect to FIGS. 10A and 10B, a shaft with a distal opening at a distal end and a locking mandrel configured to pass through a loop of an IMD proximate the distal opening, as illustrated and described with respect to FIG. 11, the shaft of FIG. 12 and/or any other feature described herein, according to particular needs.

Figure 15:
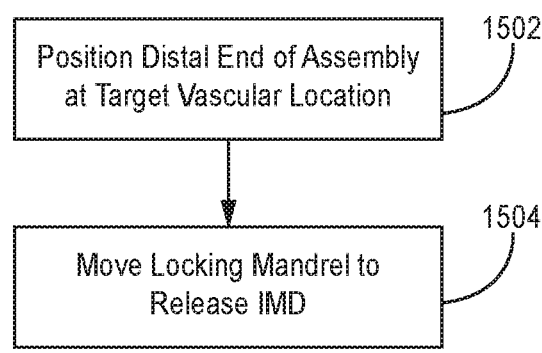
FIG. 15 is a flow diagram illustrating an example method for intravascular implantation of an implantable medical device using any of the devices of FIGS. 3A-14.

FIG. 15 is a flow diagram illustrating an example method for intravascular implantation of an implantable medical device (IMD) using any of the devices of FIGS. 3A-14. A practitioner may position a distal end of an assembly at a target vascular location for implantation of an IMD (1502). The assembly may be, for example, any of the kits described with respect to FIGS. 3A-14, including the IMD which may be secured to an elongated shaft, and a locking mandrel for securing the IMD to the shaft. Positioning the distal end of the assembly at the target location may include tracking the assembly over a guidewire to, for example, a pulmonary artery or any other suitable location. Positioning the distal end of the assembly at the target location may include visualizing a marker band at or near the distal end of assembly.

The practitioner may move the locking mandrel to release the IMD (1504). For example, the practitioner may retract the locking mandrel with respect to the shaft, may rotate the locking mandrel with respect to the shaft, or may advance the locking mandrel with respect to the shaft, as applicable, to release the IMD from the shaft. Upon release, the fixation members of the IMD may expand to fixate the IMD in the target vascular location, as described with respect to FIGS. 2A and 2B.

Additional steps may be used. For example, a practitioner may load the IMD onto the shaft. In some examples, the practitioner may use an unlock and/or lock function on a handle attached to the locking mandrel to load the sensor onto the shaft, as described in further detail above with respect to FIGS. 3A-14, and/or to retract the locking mandrel to release the IMD from the shaft. The method may further include retracting the shaft after delivery of the IMD and/or closing an entry site into the vasculature.

The following embodiments enumerated consecutively from 1 through 31 provide for various additional aspects of the present invention. In one embodiment, in a first embodiment (1), the present invention provides a kit for intravascular implantation of an implantable medical device within a patient, the kit comprising:

the implantable medical device comprising a fixation assembly comprising a loop;

an elongated shaft defining at least one longitudinal lumen and a port in fluid communication with the lumen, the shaft sized to traverse a vasculature of the patient and the port sized to receive at least a portion of the loop of the fixation assembly of the implantable medical device; and a locking mandrel configured to be positioned within the at least one lumen of the shaft and configured to pass through the loop of the fixation assembly of the implantable medical device within the lumen at the port, wherein a reduced profile portion of the shaft defines a reduced profile with respect to at least one other portion of the shaft, wherein at least a portion of the reduced profile portion is configured to be adjacent to the implantable medical device when the implantable medical device is positioned on the shaft.

2. The kit of embodiment 1, wherein the port comprises a proximal port and the loop comprises a first loop of the fixation assembly of the implantable medical device, wherein the elongated shaft further defines a distal port in fluid communication with the lumen and sized to receive at least a portion a second loop of the fixation assembly of the implantable medical device, each of the proximal port and the distal port being defined on a side wall of the elongated shaft.

3. The kit of embodiment 2, wherein the proximal port is circumferentially spaced approximately 180 degrees about the elongated shaft from the distal port.

4. The kit of any of embodiments 1 to 3, wherein the locking mandrel defines a guidewire lumen configured for passage of a guidewire.

5. The kit of any of embodiments 1 to 4, wherein the at least one lumen of the elongated shaft is configured such that a guidewire and the locking mandrel may be positioned adjacent to one another within the at least one lumen.

6. The kit of any of embodiments 1 to 5, wherein the elongated shaft comprises a locking shaft defining the port and a guidewire shaft, wherein the locking shaft defines a locking lumen configured to receive the locking mandrel, wherein and the guidewire shaft defines a guidewire lumen configured to receive a guidewire, wherein the locking shaft is twisted about the guidewire shaft.

7. The kit of any of embodiments 1 to 6, wherein the locking mandrel comprises at least one helical portion, wherein the locking mandrel is configured to be rotated with respect to the shaft to pass through the loop of the fixation assembly.

8. The kit of any of embodiments 1 to 7, wherein the port comprises a first port and the shaft defines a second port, wherein the second port is configured to receive at least a portion of a housing of the implantable medical device, wherein the locking mandrel is configured to pass through a lumen defined by the housing of the implantable medical device at the second port.

9. The kit of any of embodiments 1 to 8, wherein the reduced profile portion is configured to be positioned between two cleats of the implantable medical device when the implantable medical device is positioned on the shaft.

10. The kit of any of embodiments 1 to 9, wherein the shaft comprises the reduced profile portion, a proximal portion proximal to the reduced profile portion, and a distal portion distal to the reduced profile portion, wherein each of the reduced profile portion, the proximal portion, and the distal portion comprise a respective portion of an inner shaft, wherein the proximal portion comprises a proximal outer shaft configured to surround at least a first portion of the inner shaft, wherein the distal portion comprises a distal outer shaft configured to surround at least a second portion of the inner shaft.

11. A kit for intravascular implantation of an implantable medical device within a patient, the kit comprising:

an elongated shaft defining at least one longitudinal lumen and a port in fluid communication with the lumen, the shaft sized to traverse a vasculature of the patient and the port sized to receive at least a portion of a loop of a fixation assembly of the implantable medical device; and a locking mandrel configured to be positioned within the at least one lumen of the shaft and configured to pass through the loop of the fixation assembly of the implantable medical device within the lumen at the port.

12. The kit of embodiment 11, wherein the port comprises a proximal port and the loop comprises a first loop of the fixation assembly of the implantable medical device, wherein the elongated shaft further defines a distal port in fluid communication with the lumen and sized to receive at least a portion a second loop of the fixation assembly of the implantable medical device, each of the proximal port and the distal port being defined on a side wall of the elongated shaft.

13. The kit of embodiment 12, wherein the proximal port is circumferentially spaced approximately 180 degrees about the elongated shaft from the distal port.

14. The kit of any of embodiments 11 to 13, wherein the locking mandrel defines a guidewire lumen configured for passage of a guidewire.

15. The kit of any of embodiments 11 to 14, wherein the at least one lumen of the elongated shaft is configured such that a guidewire and the locking mandrel may be positioned adjacent to one another within the at least one lumen.

16. The kit of any of embodiments 11 to 15, wherein the elongated shaft comprises a locking shaft defining the at least one port and a guidewire shaft, wherein the locking shaft defines a locking lumen configured to receive the locking mandrel, wherein and the guidewire shaft defines a guidewire lumen configured to receive a guidewire, wherein the locking shaft is twisted about the guidewire shaft.

17. The kit of any of embodiments 11 to 16, wherein the locking mandrel comprises at least one helical portion, wherein the locking mandrel is configured to be rotated with respect to the shaft to pass through the loop of the fixation assembly.

18. The kit of any of embodiments 11 to 17, wherein the port comprises a first port and the elongated shaft defines a second port, wherein the second port is configured to receive at least a portion of a housing of the implantable medical device, wherein the locking mandrel is configured to pass through a lumen defined by the housing of the implantable medical device at the second port.

19. The kit of any of embodiments 11 to 18, wherein a reduced profile portion of the shaft defines a reduced profile with respect to at least one other portion of the shaft, wherein at least a portion of the reduced profile portion is configured to be adjacent to the implantable medical device when the implantable medical device is positioned on the shaft.

20. The kit of any of embodiments 11 to 19, wherein the reduced profile portion is configured to be positioned between two cleats of the implantable medical device when the implantable medical device is positioned on the shaft.

21. The kit of any of embodiments 11 to 20, wherein the shaft comprises the reduced profile portion, a proximal portion proximal to the reduced profile portion, and a distal portion distal to the reduced profile portion, wherein each of the reduced profile portion, the proximal portion, and the distal portion comprise a respective portion of an inner shaft, wherein the proximal portion comprises a proximal outer shaft configured to surround at least a first portion of the inner shaft, wherein the distal portion comprises a distal outer shaft configured to surround at least a second portion of the inner shaft.

22. The kit of any of embodiments 11 to 21, further comprising the implantable medical device.

23. A method for intravascular implantation of an implantable medical device within a patient comprising:
positioning a distal end of an assembly at a target vascular location for implantation of an implantable medical device, the assembly including:
the implantable medical device comprising a fixation assembly comprising a loop;
an elongated shaft defining at least one longitudinal lumen and a port in fluid communication with the lumen, the shaft sized to traverse a vasculature of the patient and the port sized to receive at least a portion of the loop of the fixation assembly of the implantable medical device; and
a locking mandrel positioned within the at least one lumen of the shaft and passing through the loop of the fixation assembly of the implantable medical device within the lumen at the port; and
moving the locking mandrel to release the implantable medical device.

24. The method of embodiment 23, wherein the port comprises a proximal port, wherein the at least one port further comprises a distal port, each of the proximal port and the distal port being defined on a side wall of the elongated shaft.

25. The method of any of embodiments 23 to 24, wherein a reduced profile portion of the shaft defines a reduced profile with respect to at least one other portion of the shaft, wherein at least a portion of the reduced profile portion is configured to be adjacent to the implantable medical device when the implantable medical device is positioned on the shaft.

26. The method of embodiment 25, wherein the reduced profile portion is configured to be positioned between two cleats of the implantable medical device when the implantable medical device is positioned on the shaft.

27. The method of embodiment 25, wherein the shaft comprises the reduced profile portion, a proximal portion proximal to the reduced profile portion, and a distal portion distal to the reduced profile portion, wherein each of the reduced profile portion, the proximal portion, and the distal portion comprise a respective portion of an inner shaft, wherein the proximal portion comprises a proximal outer shaft configured to surround at least a first portion of the inner shaft, wherein the distal portion comprises a distal outer shaft configured to surround at least a second portion of the inner shaft.

28. The method of any of embodiments 23 to 27, wherein the implantable medical device comprises a sensor.

29. A kit for intravascular implantation of an implantable medical device within a patient, the kit comprising:
an elongated shaft defining at least one longitudinal lumen and a distal opening of the at least one longitudinal lumen at a distal end of the shaft, the shaft sized to traverse a vasculature of the patient; and
a locking mandrel configured to be positioned within the at least one lumen of the shaft and defining a hook configured to pass through a loop of a fixation assembly of the implantable medical device proximate the distal opening.

30. The kit of embodiment 29, wherein the locking mandrel is configured to be advanced with respect to the shaft to release the implantable medical device from the shaft.

31. A kit for intravascular implantation of an implantable medical device within a patient, the kit comprising:
the implantable medical device comprising a fixation assembly comprising a first loop and a second loop;
an elongated shaft defining at least one longitudinal lumen, a proximal port in fluid communication with the lumen, and a distal port in fluid communication with the lumen, the shaft sized to traverse a vasculature of the patient, the proximal port sized to receive at least a portion of the first loop of the fixation assembly of the implantable medical device, the distal port sized to receive at least a portion of the second loop of the fixation assembly of the implantable medical device, each of the proximal port and the distal port being defined on a side wall of the elongated shaft, the proximal port being circumferentially spaced approximately 180 degrees about the elongated shaft from the distal port; and
a locking mandrel configured to be positioned within the at least one lumen of the shaft and configured to pass through the first loop of the fixation assembly of the implantable medical device within the lumen at the proximal port and to pass through the second loop of the fixation assembly of the implantable medical device within the lumen at the distal port,
wherein a reduced profile portion of the shaft defines a reduced profile with respect to at least one other portion of the shaft, wherein at least a portion of the reduced profile portion is configured to be adjacent to the implantable medical device when the implantable medical device is positioned on the shaft.

Various examples have been described. For example, a variety of example kits for delivery of an IMD to a target location within the vasculature of a patient have been described. Although described as separate examples with respect to a respective one or more figures, such description was not intended to be limiting with respect to inclusion of any combination of features herein in a kit. Features described with respect to any one of the example kits may be incorporated into any one or more other of the example kits, and this description should be considered to support any such combination. These and other examples are within the scope of the following claims.

What is claimed is:

1. A kit for intravascular implantation of an implantable medical device within a patient, the kit comprising:
   the implantable medical device comprising a device housing and a fixation assembly comprising a loop;
   an elongated shaft having a distal portion and defining at least one longitudinal lumen and having a port located proximal to the distal portion and in fluid communication with the lumen, the shaft sized to traverse a vasculature of the patient and the port sized to receive at least a portion of the loop of the fixation assembly of the implantable medical device; and
   at least one locking mandrel configured to be positioned within the at least one lumen of the shaft, configured to pass through the loop of the fixation assembly of the implantable medical device while the device housing is located exterior to the shaft and proximal to the distal portion thereof and the portion of the loop is located within the port, and configured to extend within the at least one lumen distally from the port and from the portion of the loop therein,
   wherein a reduced profile portion of the shaft defines a reduced profile with respect to at least one other portion of the shaft, wherein at least a portion of the reduced profile portion is configured to be adjacent to the device housing when the implantable medical device is positioned on the shaft; and
   wherein the elongated shaft comprises a locking shaft defining the port and a guidewire shaft, wherein the locking shaft defines a locking lumen configured to receive the locking mandrel, wherein the guidewire shaft defines a guidewire lumen configured to receive a guidewire, wherein the locking shaft is twisted about the guidewire shaft.

2. The kit of claim 1, wherein the port comprises a first port and the shaft defines a second port, wherein the second port is configured to receive at least a portion of a housing of the implantable medical device, wherein the locking mandrel is configured to pass through a lumen defined by the housing of the implantable medical device at the second port.

3. The kit of claim 1, wherein the at least one lumen of the elongated shaft is configured such that a guidewire and the locking mandrel may be positioned adjacent to one another within the at least one lumen.

4. A kit for intravascular implantation of an implantable medical device within a patient, the kit comprising:
   the implantable medical device comprising a device housing and a fixation assembly comprising a loop;
   an elongated shaft having a distal portion and defining at least one longitudinal lumen and having a port located proximal to the distal portion and in fluid communication with the lumen, the shaft sized to traverse a vasculature of the patient and the port sized to receive at least a portion of the loop of the fixation assembly of the implantable medical device; and
   at least one locking mandrel configured to be positioned within the at least one lumen of the shaft, configured to pass through the loop of the fixation assembly of the implantable medical device while the device housing is located exterior to the shaft and proximal to the distal portion thereof and the portion of the loop is located within the port, and configured to extend within the at least one lumen distally from the port and from the portion of the loop therein; and
   wherein the elongated shaft comprises a locking shaft defining the port and a guidewire shaft, wherein the locking shaft defines a locking lumen configured to receive the locking mandrel, wherein the guidewire shaft defines a guidewire lumen configured to receive a guidewire, wherein the locking shaft is twisted about the guidewire shaft.

5. The kit of claim 4, wherein the port comprises a proximal port and the loop comprises a first loop of the fixation assembly of the implantable medical device, wherein the elongated shaft further defines a distal port in fluid communication with the at least one lumen and sized to receive at least a portion a second loop of the fixation assembly of the implantable medical device, each of the proximal port and the distal port being defined on a side wall of the elongated shaft.

6. The kit of claim 5, wherein the proximal port is circumferentially spaced approximately 180 degrees about the elongated shaft from the distal port.

7. The kit of claim 4, wherein the port comprises a first port and the shaft defines a second port, wherein the second port is configured to receive at least a portion of a housing of the implantable medical device, wherein the locking mandrel is configured to pass through a lumen defined by the housing of the implantable medical device at the second port.

* * * * *